US008813566B2

(12) United States Patent
Fitzpatrick

(10) Patent No.: US 8,813,566 B2
(45) Date of Patent: Aug. 26, 2014

(54) INSTRUMENTATION AND ANALYTICAL TECHNIQUES SUITABLE FOR BROADBAND ACOUSTIC RESONANCE DISSOLUTION SPECTROSCOPY

(75) Inventor: Dara Fitzpatrick, Cork (IE)

(73) Assignee: University College Cork—National University of Ireland, Cork (IE)

( * ) Notice: Subject to any disclaimer, the term of this patent is extended or adjusted under 35 U.S.C. 154(b) by 519 days.

(21) Appl. No.: 12/988,747

(22) PCT Filed: Apr. 21, 2009

(86) PCT No.: PCT/EP2009/054734
§ 371 (c)(1),
(2), (4) Date: Jan. 3, 2011

(87) PCT Pub. No.: WO2009/130214
PCT Pub. Date: Oct. 29, 2009

(65) Prior Publication Data
US 2011/0088471 A1    Apr. 21, 2011

(30) Foreign Application Priority Data

Apr. 21, 2008   (IE) .................................. 2008/0308

(51) Int. Cl.
*G01N 29/036*   (2006.01)
*G01N 29/14*    (2006.01)
(52) U.S. Cl.
USPC .............................................. 73/579; 73/587
(58) Field of Classification Search
CPC ..... G01H 13/00; G01H 29/12; G01H 29/022; G01H 29/036; G01H 2291/0256

USPC ...................................................... 73/579, 587
See application file for complete search history.

(56) References Cited

U.S. PATENT DOCUMENTS

| | | | | | |
|---|---|---|---|---|---|
| 2,350,534 | A | * | 6/1944 | Rosinger | ........................ 366/274 |
| 5,152,180 | A | * | 10/1992 | Waldhauer, Jr. | ................. 73/579 |
| 5,656,428 | A | | 8/1997 | McAllister et al. | |
| 2002/0003385 | A1 | * | 1/2002 | Jones | ............................ 310/334 |

FOREIGN PATENT DOCUMENTS

EP    1847830 A1    10/2007

OTHER PUBLICATIONS

International Search Report and Written Opinion: Application No. PCT/EP2009/054734, ISA/European Patent Office, Sep. 9, 2009.
Crawford, Frank S., "The Hot Chocolate Effect," Am J. Phys., 50(5), 1982.
Christopher S. Towler et al., "Impact of Molecular Speciation on Crystal Nucleation in Polymorphic Systems: The Conundrum of c Glycine and Molecular Self Poisoning", J. Am. Chem. Soc. 2004, 126, pp. 13347-13353.

(Continued)

*Primary Examiner* — Hezron E Williams
*Assistant Examiner* — Gregory J Redmann
(74) *Attorney, Agent, or Firm* — Schmeiser, Olsen & Watts LLP; Lowell W. Gresham; Charlene R. Jacobsen

(57) ABSTRACT

A new analytical technique, instrument and method of testing a material utilizing same is provided. The method of analyzing a test material comprises the steps of (vii) inducing an acoustic emission from a vessel containing a solvent and measuring said emissions; (viii) dissolving a known amount of the test material in the solvent; measuring changes in resonance and absorbance frequencies before and after dissolution to produce a broadband acoustic resonant dissolution emission profile.

20 Claims, 22 Drawing Sheets

(56) References Cited

OTHER PUBLICATIONS

Isabelle Weissbuch et al.,"Solvent Effect on Crystal Polymorphism: Why Addition of Methanol or Ethanol to Aqueous Solutions Induces the Precipitation of the Least Stable b Form of Glycine" "Chem", 2005, 117, pp. 3290-3293.

F. Crawford, "Hot water, Fresh Beer and Salt", American Journal of Physics, Nov. 1990, vol. 58, Issue 11, pp. 1033.

* cited by examiner

NaCl (1.37M) Gas Saturation Profiles

NaCl (1.37M) Air profiles

NaCl (1.37 M) Air Saturation profiles 4g salt comparison 6g salt comparison 6g salt comparison 1.37M Salt Comparison 1.37M Salt Comparison NaCl Crossover Analysis KBR Crossover analysis $Na_2CO_3$ crossover Analysis Salt crossover comparison plot Salt crossover comparison plot NaCl Particle Size Comparison NaCl Particle Size Comparison NaCl Particle Size Comparison Sucrose particle size plot Copper Sulphate pseudopolymorphs

INSTRUMENTATION AND ANALYTICAL TECHNIQUES SUITABLE FOR BROADBAND ACOUSTIC RESONANCE DISSOLUTION SPECTROSCOPY

FIELD OF THE INVENTION

The invention relates to analytical techniques and instrumentation utilising such techniques. Applications including qualitative analysis, quantitative analysis, particle sizing, polymorph analysis, porosimetry, mixtures analysis, isomer analysis, and racemic mixtures analysis are possible using this technique.

BACKGROUND TO THE INVENTION

Acoustic sound relates to frequencies of sound that are perceptible to the human ear (20 Hz and 20 kHz). Acoustics is the scientific study of the behaviour of mechanical sound waves in various forms of matter, e.g. gases, liquids and solids. Like any mechanical or energy wave, moving acoustic wave fronts can be refracted or reflected as they encounter a new medium. In the same way light is refracted on moving from an air or liquid medium to a glass medium, sound waves are refracted on moving from an air or liquid medium to a glass one. Interestingly and importantly for the present invention, sound waves, unlike light (which moves linearly), propagate spherically; thus the orientation of a detecting means to the sound source in the system under study is relatively inconsequential, as the acoustic data contained in energy that reaches the detecting means contains all the data of the total system. Typically a microphone is used to detect and record the sound profiles.

Sonochemistry, the chemistry of sound, generally refers to the use of sound, principally ultrasound (sound above 20 kHz), to trigger chemical reactions which are difficult to achieve under normal atmospheric conditions. In simple terms BARDS technology is a new direct method of monitoring the liberation and subsequent release of dissolved gases from solution during the dissolution of a solute. It must be stressed that the platform presented herein has little, if any, connection to sonochemistry, where ultrasound is actively used to drive reactions or monitor their progression.

Minor investigations were carried out on the acoustic effect of dissolving a solute into a liquid (W. Bragg et al) in the 1930s. Further investigations were made by F. Crawford and details were published in his papers "*The Hot Chocolate Effect* (1981)" and "*Hot water, Fresh Beer and Salt* (1985)". They described the acoustic effect as resulting from a decrease in the resonant tone of the glass, followed by a prolonged increase in the tone. The effect was linked to the formation of microscopic bubbles in solution. These bubbles are thought to generate as a result of the addition of a solute, which through dissolution, forces a proportional quantity of gas out of solution.

The so called "Hot Chocolate Effect" is a phenomenon of wave mechanics, where the pitch heard when a cup of hot liquid is tapped, rises after the addition of a soluble powder.[1] The "Hot Chocolate Effect" works for any liquid in which a gas is soluble. When the vessel containing the liquid is tapped to resonate and a solute is introduced, it is observed that the velocity of sound in the liquid is reduced below that of bubble-free liquid and the pitch of the emitted sound is correspondingly reduced. As the bubbles liberated by the dissolving solute float to the top of the vessel, a smaller fraction of the volume has reduced sound velocity and so the pitch rises, until eventually the pitch corresponds to that of bubble-free liquid wherein the majority of the bubbles have floated to the top.

Crawford postulated that the bubbles, at first homogeneously distributed throughout the solution, begin to rise and create a layer of bubble-filled liquid, which gradually reduces in size as the bubbles exit the liquid phase through the surface. The gradual increase in pitch results from the reduction of the bubble layer, or rather the increasing volume of liquid unaffected by desolvating gas. This allows sound to travel faster through the clear layer, due to lower compressibility, thus producing a higher pitched note. Eventually all produced gas, due to desolvation, is eliminated from solution and the resonant frequencies of the vessel return to steady state.

As a solute dissolves in a solution, the solubility of dissolved gases reduces. The velocity of sound is reduced as the gas bubbles exit the solution with a corresponding reduction in frequency (pitch). Crawford noted that two opposing parameters control this phenomenon: mass density "e" (inertial property) and compressibility "c" (elastic property). Sound travels more slowly the greater the mass density of the gas or liquid, e.g. sound travels faster in helium than it does in air. However, greater compressibility of a medium also results in the reduced velocity of sound.

Even though the inertial factor favours gases, the elastic factor has a greater influence on the speed (v) of a wave. Therefore, the velocity of sound in a solid>velocity in liquid>velocity in gases according to the following equation:

$$v = 1/\sqrt{e \cdot c} \qquad \text{Equation 1}$$

where v=velocity, e=mass density, and c=compressibility of the liquid. Aqueous solutions have a mass density 800 times that of air that imparts a reduced sound velocity compared to air based on inertial properties. In comparison, air is 15,000 times more compressible than water, thus air carries sound more slowly by a factor of 4.3. In a solution containing gas bubbles, the two factors combine to significantly reduce the speed of sound. This is due to the greater mass density of the solution, which also has temporarily the compressibility of a gas.

The effect is also observed in hot liquids, e.g., when air under high pressure in a solution of hot water comes out of solution, it forms bubbles. The greater the air in the form of bubbles in the solution, the lower the pitch of sound emitted when a vessel holding the water is tapped continuously to allow the vessel to resonate. No effect is observed when cold water is used. This is because the dissolved air stays in solution.

To date, despite the phenomena being known for some time, no analytical techniques have been developed to make use of the effect.

Therefore, it is desirable to provide new, versatile methods of materials analysis capable of employing broadband resonance spectroscopy and an analytical instrument to carry out such analysis.

SUMMARY OF THE INVENTION

According to the present invention, as set out in the appended claims, there is provided a method of analysing a test material comprising the steps of:
 (i) inducing an acoustic emission from a vessel containing a solvent and measuring said emissions;
 (ii) dissolving a known amount of the test material in the solvent;

(iii) measuring changes in resonance and absorbance frequencies before and after dissolution to produce a broadband acoustic resonant dissolution emission profile.

This novel methodology allows spectroscopic analysis of broadband acoustic resonance effects and forms the basis for a new platform analytical technology based on monitoring the acoustic sound profile and resonant changes of a vessel during the dissolution of various compounds in aqueous solution. More particularly, the technique is based on the phenomena observed, that on addition of a solute to a solvent, the resonant frequencies of the vessel containing the solution decrease significantly and gradually return to, or close to, the original frequency after the substances reach the point of complete dissolution.

Thus, the method, and an instrument of the invention using such method, finds application across the scientific spectrum, but is of particular use in the chemical and pharmaceutical industries. Thus, the invention provides a powerful technique and a sensitive instrument designed to utilise said phenomena.

Advantageously, the invention provides an analytical instrument that is compact, relatively inexpensive to provide and easy to use. Further advantageous arise from the fact that the invention provides an instrument that is capable of determining particle size distributions, differentiating between polymorphs, and differentiating between isomers and the analysis of mixtures of compounds and their ratios in solution.

Suitably, the vessel may be of any resonant material. However, in a preferred embodiment, the vessel may be comprised of glass. The solvent may be any liquid. However, it is preferable to employ water, since advantageously, water is non-toxic, plentiful, cheap and is capable of dissolving many substances. Mixtures or aqueous solutions of other liquids/substances may equally well used, depending on the solubility properties of the test material in question. One or more individual resonant and absorbance frequencies may be monitored, however in a preferred embodiment, it is preferable to monitor and measure changes in all resonant and absorbance frequencies.

Suitably, the solvent may be used with or without prior treatment such as de-aeration or sonication.

In a preferred embodiment, the solvent contains dissolve gas. Suitably, the gas may be air or other gases such as nitrogen, helium, argon, neon, xeon or other dissolvable gases. Inert gases are preferred since they will not react with the test material. In a preferred embodiment, air is particular preferred since it is readily available and relatively inexpensive to provide. It is worth noting that the solvent does not have to be fully gas saturated, as long as the solvent solutions are equilibrated in the same ambient environment.

In another preferred embodiment, the test material may be a solid particulate. However, the analyte does not necessarily need to be soluble (for example silica data is presented later). Suitably, the test sample particles may preferably be in the size range of approximately 5-355 microns. However, it is expected that the technique will operate well at larger particles sizes. In fact, all that is required is that the material is in a powdered form that facilitates dissolution. In a different preferred embodiment, the test sample may be in the liquid state. There is no requirement for the sample to have a particular particle size range distribution.

It is preferably to add the sample all at once from a weighing boat or sample delivery vehicle. This ensures a timelier dissolution event and facilitates reproducibility.

Suitably, the amount of test material dissolved should be sufficient to elicit an acoustic spectrum or to alter the acoustic spectrum of a standard. In other words, the test sample should be concentrated enough to produce a response, or if introduced in a small quantity, be sufficient to alter the spectrum of a well-characterised standard, such as sodium chloride.

In a preferred embodiment, the method further comprises the step of comparing the test material broadband acoustic resonant dissolution emission profile to that of a known standard. This can be achieved by comparing the fundamental acoustic profile and/or the unique cross-over points of the overtone/harmonic resonant lines.

In a particular aspect, the method may used to differentiate between, for example, hydrated species and mixtures thereof, material particle sizes, isomers and/or epimers.

In a related embodiment there is provided an instrument for measuring the broadband acoustic resonance dissolution emission response of a test material comprising:
(i) a dissolution vessel in which the test material can be dissolved in a solvent;
(ii) a means for inducing acoustic emission from the vessel;
(iii) a means for measuring the broadband acoustic resonance dissolution emission response of the dissolution vessel over a the course of the dissolution event.

In a preferred embodiment, the instrument further comprises a means to convert the acoustic dissolution emission response from acoustic to plot data.

Suitably, the instrument may comprise a means for inducing vessel acoustic emission. In a preferred embodiment, the means comprises a stir bar. In a preferred embodiment, the means for measuring the broadband acoustic resonance dissolution emission response may comprise a microphone transducer. However, modifications may be made to the system by providing another transducer attached to the glass to provide broadband white noise or to propagate the resonant frequencies of the vessel, which would replace the mechanical propagation of resonant frequencies provided by the magnetic stirring bar.

Preferably, the means for measuring the broadband acoustic resonance dissolution emission response may be removably mounted on said vessel, however in a particular embodiment, it may be positioned beside the vessel or may be in intimate contact therewith. Advantageously, securing the microphone above the volume line delivers a better spectrum and the distances aid in reproducibility.

Suitably, the vessel may comprise glass or any resonant material. By resonant material, it is meant a material that has a tendency to oscillate at maximum amplitude at particular frequencies. Such frequencies are known as the materials resonant frequencies. During resonance, small forces can produce large amplitude vibrations.

In a related aspect, there is provided a method of calibrating a broadband acoustic resonance dissolution emission instrument for use in a broadband acoustic resonance dissolution emission spectroscopic method comprising:
(i) inducing an acoustic emission from a vessel containing a solvent;
(ii) dissolving at least one known amount of a test material in a dissolution vessel to produce a broadband acoustic resonance dissolution emission; and
(iii) measuring changes to said broadband acoustic resonance dissolution emission of the vessel as the material dissolves,
wherein the response is indicative of the amount of material dissolved.

In a preferred embodiment, the resonant acoustic dissolution emission response may be measured for at least two known amounts of the material.

In a particularly preferred embodiment, the broadband acoustic resonance dissolution emission response may be measured for at least three different known amounts of the material.

In any of these aspects, each of the broadband resonant acoustic dissolution emission responses may be plotted against the amount of test material dissolved to produce a calibration curve for use in the quantitative analysis of unknown amounts of a test material.

In a preferred embodiment, the solvent may be gas saturated. However, any solvent with dissolved gas may be expected to work, e.g., ratios of water and ethyl lactate (70:30 respectively) produce acoustic profiles. Moisture content of solvents may be estimated e.g. adding acetonitrile to water will illicit an acoustic spectrum which varies with the moisture content of the acetonitrile.

Suitably, the gas may be argon, nitrogen or helium or other dissolvable gas. Preferably inert gases should be used, since any inert gas is unlikely to react with the test material.

Suitably, the test material may be a particulate of approximate size range 5-355 microns.

In a preferred embodiment, the amount of test material dissolved may be in the range appropriate to induce an acoustic profile. This amount is generally in gram quantities but may be as low as $10^{-3}$ M in the case of pantathenic acid (Vit $B_5$).

BRIEF DESCRIPTION OF THE DRAWINGS

The invention will be more clearly understood from the following description with reference to the accompanying drawings, in which:—

DETAILED DESCRIPTION OF THE INVENTION

It has been found that a dissolution acoustic profile (FIG. 2) is characteristically related to the solute used to induce the effect. Dissolution acoustic profiles have been found to be distinct and thus profile differences can be exploited analytically. Thus, a new method for examining the effect and the captured dissolution acoustic profile has been established and a basic apparatus for the analytical examination of the dissolution processes has been developed. Said methods and instrument are described herein. The scope of the technique has been investigated to establish its analytical usefulness and applicability. The system utilizing said phenomena is named "Broadband Acoustic Resonance Dissolution Spectroscopy" (BARDS).

The technique was developed after the acoustic profile and resonant changes of a vessel during the dissolution of various compounds in aqueous solution were investigated. The investigations were based on observations that were made during the dissolution of compounds in solution. Such observations indicate that significant changes in the resonant frequencies of the dissolution vessel were found to occur during a dissolution event.

Figure 1A:
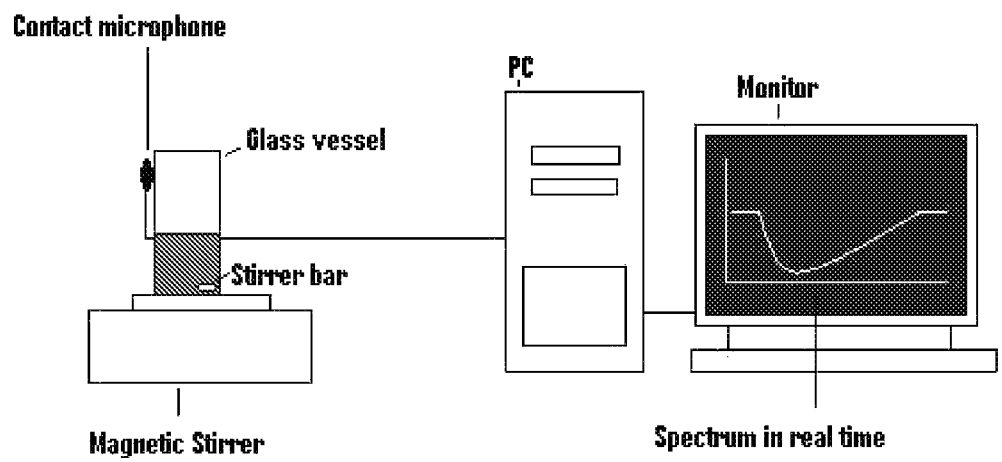
FIG. 1A: Experiment Setup. The microphone is attached by a standard jack lead directly to the PC soundcard. The spectrum can be monitored in real time as the dissolution progresses.
Figure 1B:
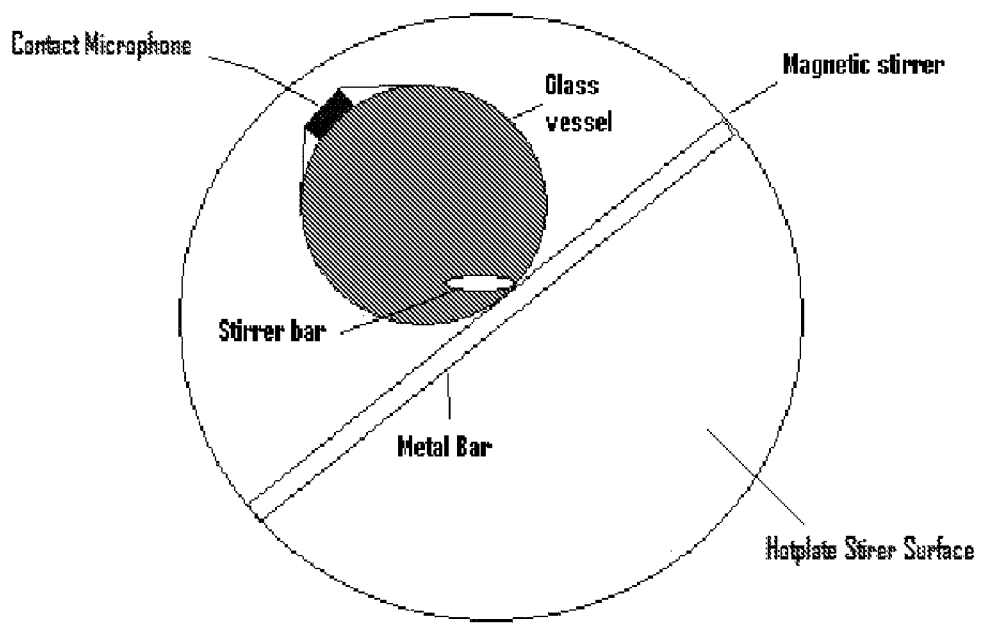
FIG. 1B: Overhead view of Glass and stirrer positioning. The glass is placed off the centre of the stirrer plate so that the stirrer bar strikes the glass side as it stirs the solution. The microphone is placed directly opposite the Stirrer bar position. A metal bar is fixed to the plate to prevent the stirrer bar moving the glass vessel forward.

It was believed that such changes could be used to qualitatively or quantitatively analyze compounds. A prototype analytical system has been designed to make use of the observed resonance changes and all indications were that such changes could form the basis of a new analytical technique. A prototype BARDS spectrometer was built around a glass dissolution vessel. This instrument is illustrated in FIGS. 1A and 1B and consists simply of a glass or other resonant material and a detection device, in this case a contact microphone placed on the vessel which in turn is placed on a magnetic stirrer.

Steady state resonance frequencies of the glass vessel are propagated at the outset of each experiment. This is achieved by allowing the magnetic stirring bar to gently tap the internal wall of the vessel. The solute is then added all at once and a dramatic change in the resonant frequencies can be seen before returning to steady state after several minutes. The frequency curve with the lowest minima is used for comparing spectra and is designated the fundamental curve.

The fundamental curves of all compounds have been found to be highly reproducible and are distinctly different such that the technique has clear qualitative and quantitative capabilities. Additionally, it has also been found that the other frequency curves have distinct cross over points which are unique to each compound and act as a fingerprint for the compound. This further highlights the qualitative ability of the technique.

Thus far, the technique has been found to be analytically useful across a range of applications. For example, the technique is capable of distinguishing between the hydrates of copper sulphate and also mixture ratios of the two. This demonstrates that the technique could also be used to quantitatively determine mixtures of two compounds using a calibration method.

Figure 23:
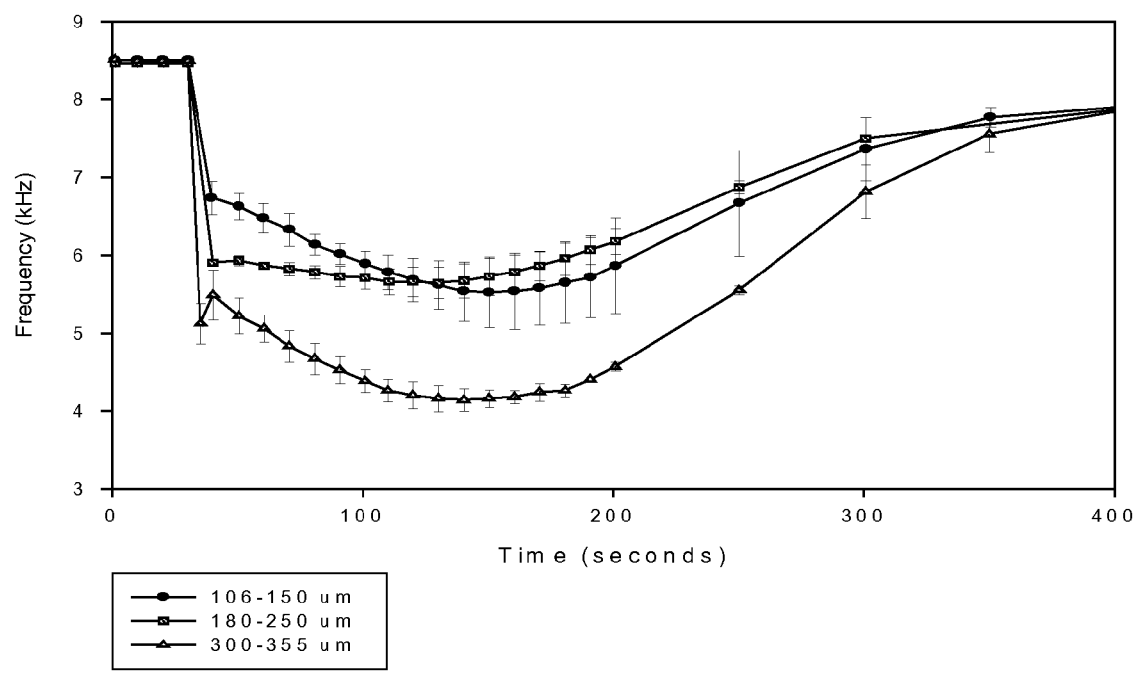
FIG. 23: Particle size distribution comparisons for sucrose (0.6M) in 100 ml of distilled water.

Similarly, it has been found that the technique is capable of carrying out particle size distribution measurements. Investigations with a number of compounds have shown that the resolution of particle size distributions is possible at defined time intervals as shown in FIG. 23. The profiles are seen to overlap; however, at the 60-100 second time interval the profiles differ significantly to allow discrimination of particle size. This represents a significant attribute of the technique.

Polymorphs of the same compound present different acoustic profiles. This is a particular advantage of the technique as the reversion of the compound from one form to another can be followed and this is an important feature for stability study monitoring of raw materials and finished products.

Figure 8:
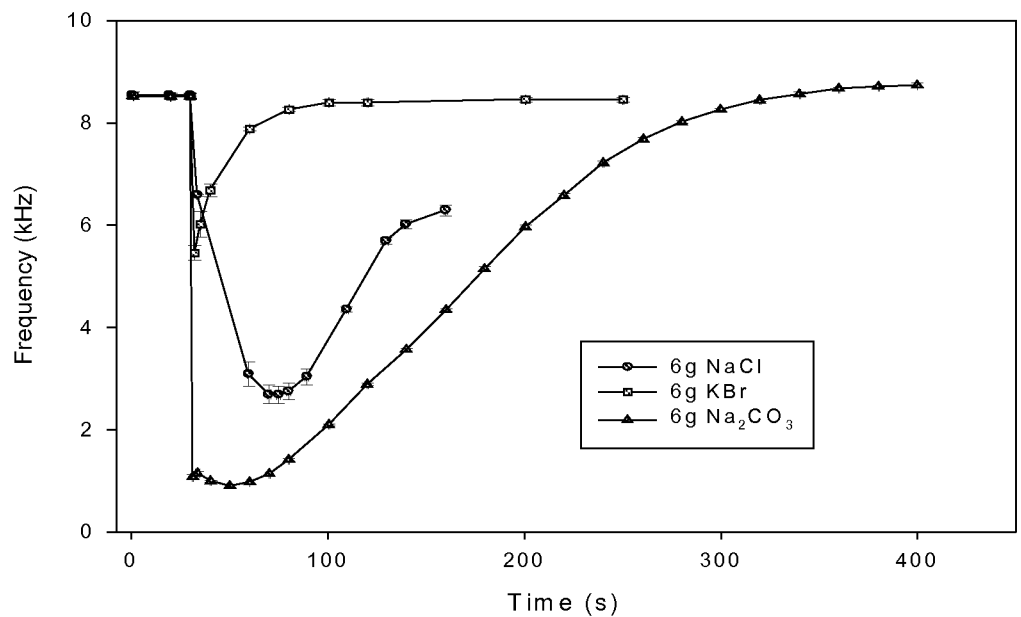
FIG. 8: Acoustic comparisons of 6 g of each salt. Note Potassium Bromide still shows no downward dissolution curve.

Isomers and epimers are also easily differentiated by the technique. These differences are important in pharmaceutical production. The difference between epimers or even a mixture of epimers are clearly discernable; this represents a further significant attribute of the technique (FIG. 8).

Further details of the scope of the methods and technique will be presented below.

Acoustic Resonance Apparatus

Figure 2:
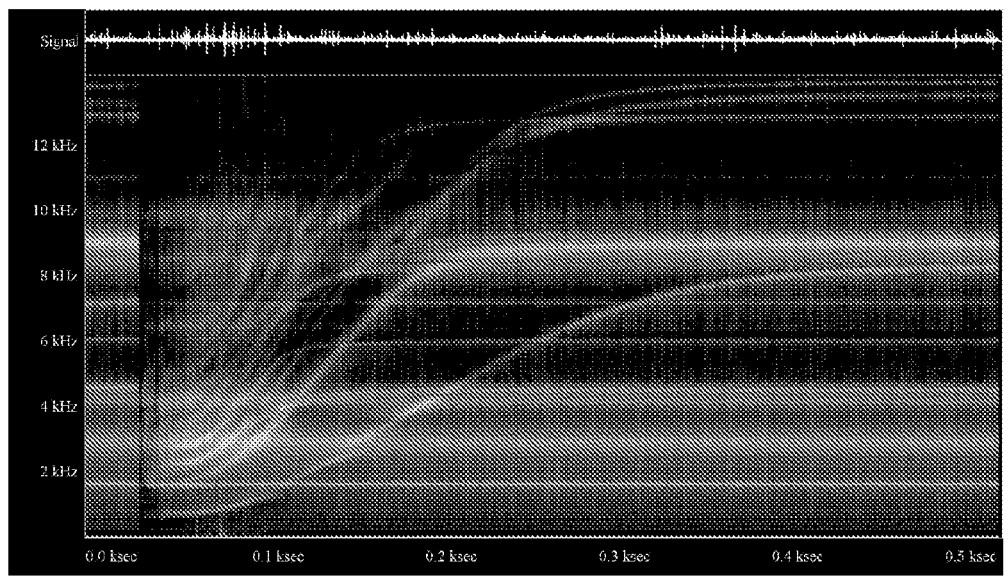
FIG. 2: Graphic Representation of the Acoustic Spectrum of the Dissolution of Sodium Carbonate

A prototype of an acoustic spectrometer was developed and used to collect data for analyses. A custom spectrometer was built around the dissolution vessel. This instrument is illustrated in FIGS. 1A and 1B and consists of a glass and contact microphone placed on a magnetic stirrer. Readily available software was used to convert the sound spectra to a graphical representation of the dissolution event. A typical dissolution profile of sodium carbonate is shown in FIG. 2. Modifications can be made to the system by providing another transducer attached to the glass to provide broadband white noise or to propagate the resonant frequencies of the vessel. This would replace the mechanical propagation of resonant frequencies provided by the magnetic stirring bar.

The initial acoustic resonance apparatus consisted of a glass vessel. A KB-26 Kingstste Piezoelectric transducer, supplied in bulk quantities from Radionics (stock number 231-2973), is attached via adhesive tape to the external side of the vessel. The transducer is wired directly into the sound card of a PC. The glass is placed on a Janke and Kunkle IKA Combimag Magnetic Stirrer. The PC was installed with sound recording software, which converts the acoustic data into digital visual information.

Heating means can also be employed, however, heating tends to alter the resonant frequencies of the glass over an extended period. However, advantageously, heating assists in dissolution or certain substances. For example, heat has been used successfully to dissolve lactic acid with the minima occurring at an earlier time point as the heat is increased.

Gas Saturation Studies Apparatus

Gas saturation studies were carried out using a Datastudio dissolved oxygen probe for all DO determinations. Argon, nitrogen and oxygen were introduced into solution via a Gibson Minipulse 3 peristaltic pump to bubble gasses through solutions.

Particle Sizing Apparatus

Particle sizing was carried out through the use of Endecott particle size sieves placed on a Pascall Sieve Shaker.

Methods and Methodology

Salt samples were hand ground to fine particulate consistency to facilitate optimum dissolution. Sodium chloride was used as a marker compound. 137 Moles (8 g) of sodium chloride yielded the optimum frequency profile, and this concentration was applied to the majority of reference compounds, only being varied when the compounds saturation level was well below this concentration.

Hydrated copper sulphate pentahydrate, was obtained by placing ground sample in a desiccator where the humidity had been increased, by placing a beaker of heated water with the sample. Anhydrous copper sulphate was obtained by drying the ground sample at 50° C. and storing in an airtight drying dessicator.

Ground sucrose was sieved and granules with particle sizes in the range 100-355 μm were retained.

An acceptable particle size distribution of test compounds was obtained by sieving for forty minutes on a 500 g loaded sieve stack consisting of an average of 10 individual sieves.

Mesh sieves and the yield of particle sizes between the individual sieves are shown in Table 1.

TABLE 1

Particle size mesh sieves used for sample particle sizing

| Sieve Mesh Size (μm) | Corresponding Size range (μm) |
|---|---|
| 25 | |
| 38 | 25-38 |
| 45 | 38-45 |
| 63 | 45-63 |
| 90 | 63-90 |
| 106 | 90-106 |
| 150 | 106-150 |
| 180 | 150-180 |
| 250 | 180-250 |
| 300 | 250-300 |
| 355 | 300-355 |

Gas Saturation of Distilled Water.

Gas saturation of distilled water was obtained using nitrogen, argon and oxygen bubbled through water (600 mls) for 20 minutes and aliquots were taken from as required. In the case of air saturation, a Gibson Minipulse peristaltic pump was set up with two rubber tubes, each connected to a glass Pasteur pipette and exposed to the open atmosphere on the other end. The rotation of the peristaltic pump was set to maximum and air was bubbled through the solution for 30 minutes before aliquots were taken for use in dissolution experiments.

Glycine Recrystallization Method

Please refer to the following publications:

1. Impact of Molecular Speciation on Crystal Nucleation in Polymorphic Systems: The Conundrum of ς Glycine and Molecular 'Self Poisoning' Christopher S. Towler,† Roger J. Davey,*,† Robert W. Lancaster,‡ and Christopher J. Price‡ J. AM. CHEM. SOC. 2004, 126, 13347-13353
2. Synthese Von Polpetiden. XIII. Chloride der Aminosauren und Polypetide und ihre Verwendung zur synthese:Emil Fishcer,
3. Solvent Effect on Crystal Polymorphism: Why Addition of Methanol or Ethanol to Aqueous Solutions Induces the Precipitation of the Least Stable b Form of Glycine
4. Isabelle Weissbuch,* Vladimir Yu. Torbeev, Leslie Leiserowitz,* and Meir Lahav* Angew. Chem. 2005, 117, 3290-3293.

General Experimental Procedure for Spectrum Collection

The inside of the glass was cleaned with distilled water whilst ensuring the outside of the glass is dry with particular care taken to prevent moisture from affecting the microphone. The microphone is placed on the outside of the glass, 5 cm above the 100 ml volume of water and 1.8 cm from the top of the glass. Securing the microphone above the volume line delivers a better spectrum and the distances aid in reproducibility. The microphone and the wire connection to the glass are secured with adhesive tape. 100 mls of distilled water is accurately poured into the glass and set stirring using a magnetic stirrer. The stirring solution is recorded for 30 seconds prior to addition of the analyte compound to record the resonant frequencies of the vessel (spectrum background). The concentration of the analyte compound is 1.37 M where saturation levels allow. The analyte compound is added carefully all at once from a weighing boat to the stirring solution, with care taken to ensure no sample is lost to the glass sides. The sample spectrum is recorded for a total of 800 seconds. Raw data was saved in .wav format files. From these files the spectrum can be replayed acoustically with any media program. This allows data points to be selected using the mouse cursor and saved in a text format file for transplantation into a data manipulation program such as Excel™ or Sigmaplot™.

Data points were selected at 5 second intervals during the initial frequency minima portion of the profile, 10 seconds for the initial return to steady state and 50 seconds for the shallow sloped portion of the steady state (usually beyond 300 seconds).

Result of Variants on Spectral Profiles

Gas Saturation Studies

Figure 3:
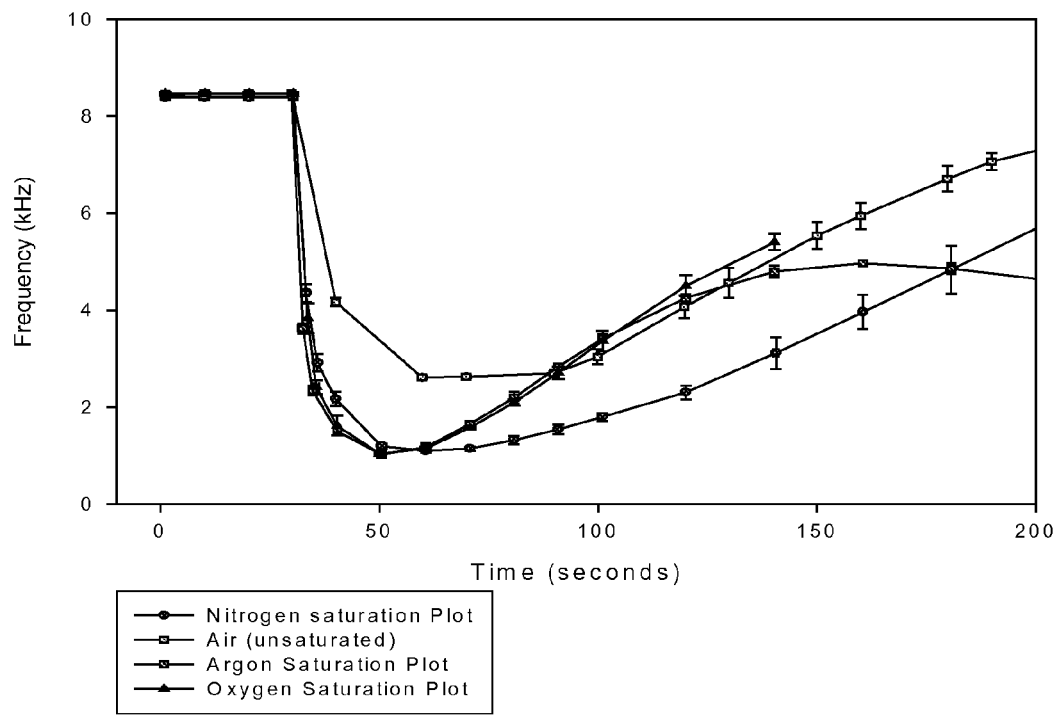
FIG. 3: Gas saturation profiles utilizing three alternate gas options, compared with a standard ambient saturation Air profile.

The graph in FIG. 3 shows the fundamental dissolution profiles for sodium chloride where the solution was saturated with different gases. All three experiments utilizing a gas other than air, differ markedly from the ambient air saturated profile. Most notably different is the nitrogen profile, which has an elongated return towards steady state. Oxygen and argon are virtually identical, with the oxygen frequency profile disappearing after 140 seconds, and the argon profile which reaches a maximum return point earlier than Nitrogen then slowly decreases in frequency again. The cause of frequency profile loss is possibly due to re-absorption of gas as it exits. Non-return to the original steady state is attributed to the degree of hygroscopicity/moisture in the sample. These experiments, although useful in illustrating the effect with different component gases of air, need to be repeated under a more controlled environment. This is due to the fact that gases can be quickly reabsorbed from the atmosphere in the timescale required to prepare the solution for the addition of the solute. However, it can be seen from the graph that the saturation profiles yield a greater minima (lower in frequency) than the ambient solution. There is a finite amount of gas which can be expelled from solution and this would appear to be increased when the solution is saturated with gas.

The data points on the minima of the profile (between 30 seconds and 100 seconds) are currently considered the most consistent and vital information points being catalogued, and as is indicated from the error bars, in each case produced from three replicate dissolutions, these are highly reproducible.

Figure 4:
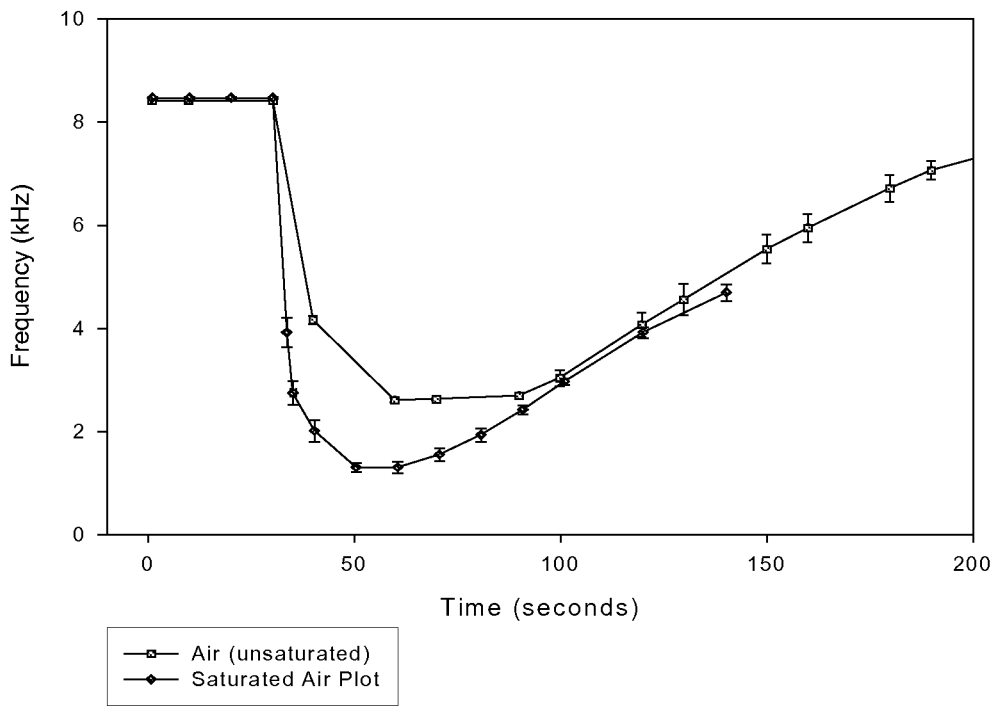
FIG. 4: Comparison of ambient air saturated distilled water with air saturated distilled water. The extent of the frequency drop is increased with the abundance of extra gas in solution, but the return path to steady state is similar after 100 s.

FIG. 4 shows the marked difference between sodium chloride profiles on standard ambient air saturated solution, which is dependent upon temperature, and water fully saturated with air. The increased depth of the frequency minima, which is approximately 1000 Hz in difference, is significant of how dependent the acoustic effect is on the level of gas in solution.

Figure 5:
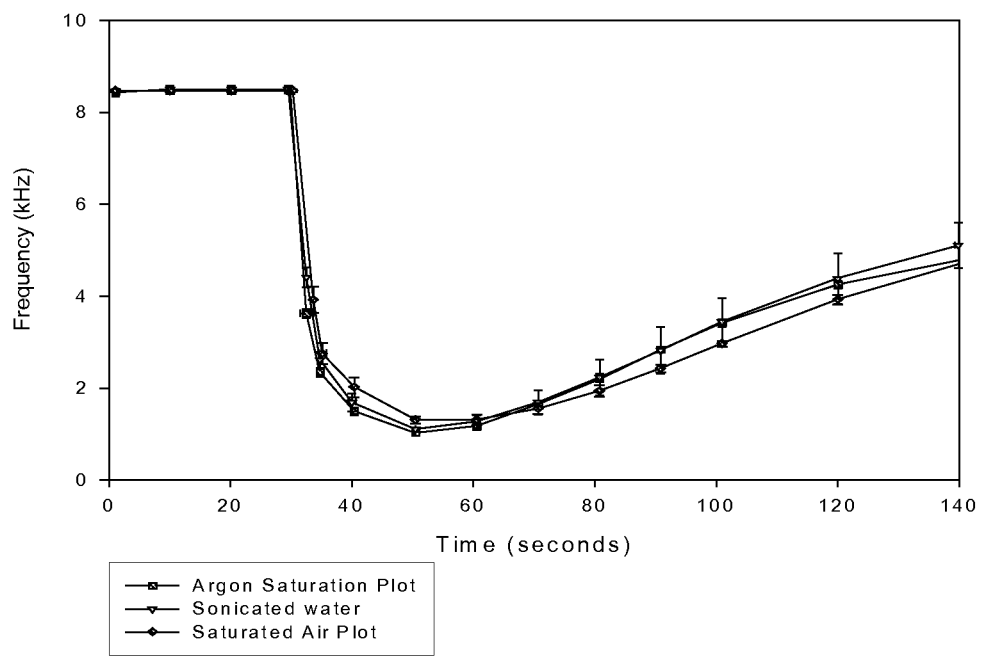
FIG. 5: 1.37 M Sodium chloride profiles utilizing both air saturated and sonicated distilled water solvents, compared with Argon saturated solution. Quite similar profiles in both the extent of the frequency drop and the distinct shape of the profile.

However FIG. 5, compares the saturated air sodium chloride profile with those of sonicated water and water which has been saturated with argon. The similarity of these profiles is somewhat puzzling, as the sonicated solution should be "gas free" after sonication. The similarities in spectra may be coincidental given the methodology used for these investigations. Sonicated solutions can rapidly reabsorb gas into solution. The hypothesis of loosely bound gas and molecularly bound (tightly bound) gas in solution may explain some of the anomalies. These results require further investigation.

Figure 6:
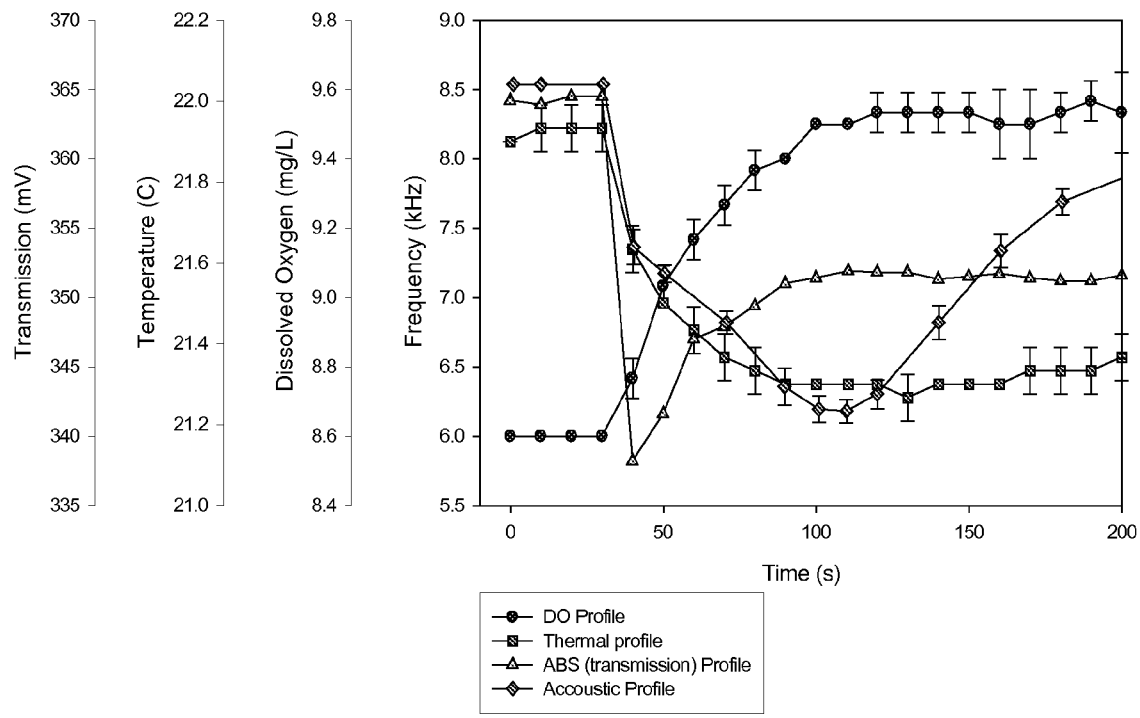
FIG. 6: Comparison of the Acoustic Resonance Profile of Copper Sulphate with its temperature, dissolved oxygen and light absorbance readings.
Figure 7:
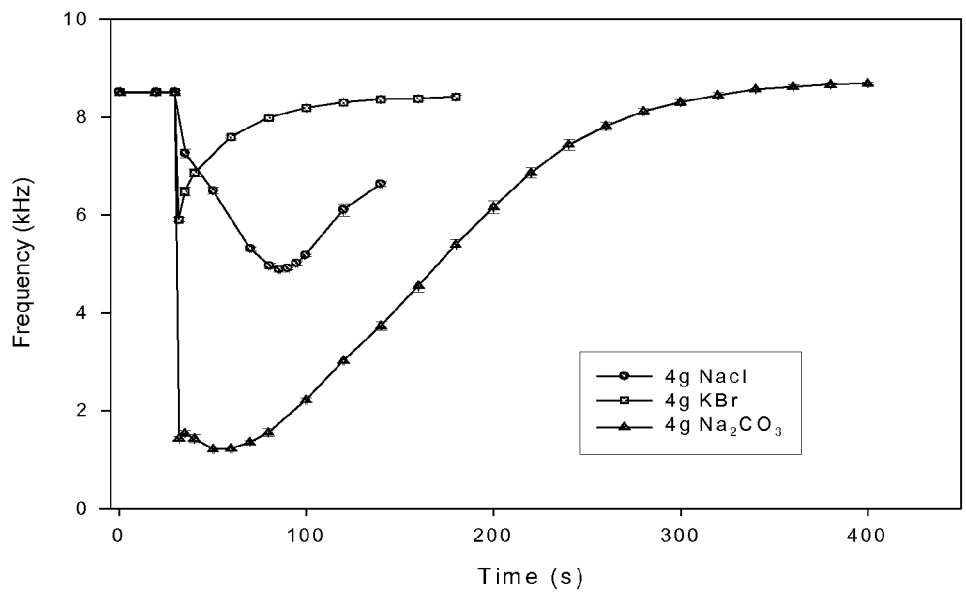
FIG. 7: Fundamental Acoustic Profiles of several compounds illustrating the qualitative capability of Acoustic Spectroscopy. Acoustic comparisons of 4 g of each salt. Note Potassium Bromide shows no downward curve at this low concentration, but a reasonably prolonged return path to steady state. This suggests that the bubble layer formed takes a definitive time period to eliminate from solution.
Figure 9:
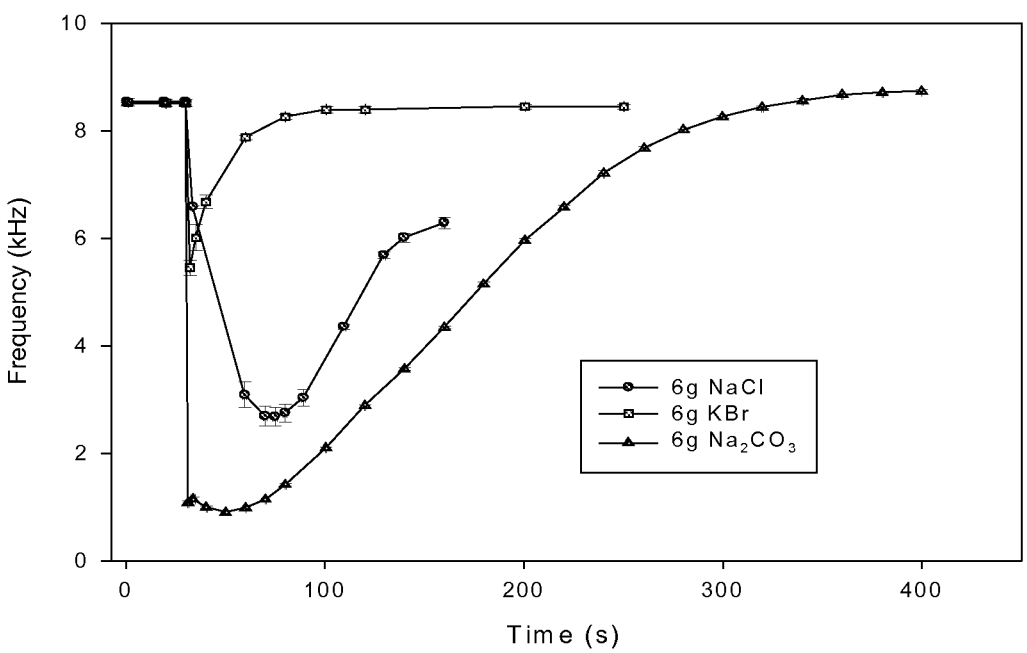
FIG. 9: Acoustic comparisons of 8 g of each salt. Potassium Bromide shows a slightly lower starting value for the beginning of the return course to steady state.

FIG. 6 compares the data for a copper sulphate pentahydrate, run at 0.4M concentration, with transmission spectrometer, thermal sensor, dissolved oxygen and acoustic data. All of the data curves reach their steady state at the same time (c.a. 110 seconds) except for the acoustic profile which reaches its minima and begins its return towards steady state. This indicates the point at which dissolution is complete. Maximum absorption of light is attained at the minima which supports this hypothesis. At this point, the exit of gases from solution exceeds the creation of gas at nucleation points and the acoustic profile begins to return to steady state This time period is both material and temperature dependent Effect of Varying Mass of Solute It was necessary to compare similar masses of the 3 ionic salts, to ensure that the unique profiles were simply not a matter of varying masses between the same concentration runs. Runs using 4, 6 and 8 grams of each salt were carried out in triplicate and compared. The results shown in FIGS. 7 to 9 show that there is no relationship between the same masses used for different salts. Therefore, for unknown samples this gives an analytical advantage as compounds will give distinct spectra when adding the same mass for dissolution.

Temperature Effects

Assessment of temperature effects is important in respect of the time period required for the profiles to attain steady state. Most temperature profiles, except those of sodium chloride, fail to return to ambient temperature within the same time frame as the acoustic profile. An acoustic profile results regardless of whether the dissolution event is endothermic or exothermic. The recovery of the temperature of the solution to ambient temperature is also independent of the dissolution event. Therefore, temperature alone is not responsible for the acoustic effect demonstrated, especially in the case of sodium chloride, where the endothermic temperature change is insignificant, compared to that of potassium bromide, which undergoes a far more significant thermal alteration, yet both salts display a similar level of frequency change in their acoustic profiles. Overall, ambient experimental temperature conditions are preferred. In fact, it has been observed for $CaSO_4$ that the frequency minima appears much sooner when the temperature is lowered to 6 degrees Celsius. This is in keeping with the dissolution behaviour of calcium sulfate which has decreasing solubility, the higher the temperature.

Hydration Effects and Pseudo Polymorphism

The effect of hydration on the acoustic profile, especially on those which are particularly hydroscopic, was observed through the use of copper sulphate pentahydrate and its anhydrous form. Ground copper sulphate pentahydrate was ground to a fine consistency, yielding a mix of both the anhydrous and pentahydrate form. A portion of the grind was dried in an oven at 50° C. until the white anhydrous form was achieved. This was allowed to equilibrate to room temperature in a dessicator.

Another portion of the grind was placed in an empty dessicator with a beaker of heated water. By humidifying the atmosphere in the dessicator to a maximum at ambient temperature, a deep blue colour of the pentahydrate form was achieved.

It is important to factor in the molecular mass of the hydrating water molecules when calculating the masses to be used in the runs of these two forms. The runs were performed at 0.4M concentrations in 100 ml of double distilled water. In the case of the 0.2M 50:50 ratio runs, 0.2M of each form was taken and mixed by stirring the pre-weighed forms in a clean beaker.

These two forms are termed "pseudo polymorphs" as they are different crystal forms of the same compound. They differ in molecular weight and composition due to the variability in hydrating water molecules. It is most interesting to note that a smaller mass of the anhydrous compound yielded the greatest deflection in the acoustic profile. The 0.4M profiles for each form differed markedly in the extent of their frequency reductions and in terms of time required to reach steady state. The time required for complete dissolution also differed, with the hydrated form reaching completion at 100 seconds and the anhydrous form reaching complete dissolution at 75 seconds. This is possibly due to the crystallized water molecules in the hydrated form acting as a barrier to the dissolution process. The combined 50:50 mix of the two forms showed that the minima of the frequency well lies between that of the pure anhydrous profile and the hydrated profile, and notably the sum of the 0.2M anhydrous form and the 0.2M hydrated form matches that of the combined 50:50 mix. This suggests that each component elicits its own unique response during the dissolution. This suggests future potential for data acquisition of a mix of solutes.

Summary

The theoretical concepts behind the acoustic dissolution phenomenon are complex and require rigorous investigation. The number of variables changing within the system during a standard dissolution event, make it difficult to assign the causes to any one parameter occurring during the dissolution. It is also difficult to monitor these variables with respect to each other.

Volume could not be monitored in real time, though the total increase at the endpoint of dissolution could easily be ascertained. However, it is known from previous publications (YihYuh et al), that volume directly affects the pitch of a glass vessel's resonance frequency. Experimental data shows that even large increases or decreases in volume, push the fundamental frequency band a small amount away from the standard 8.3 kHz at 100 ml. Therefore it is likely that the volume contribution to the overall acoustic phenomenon is insignificant.

Figure 10:
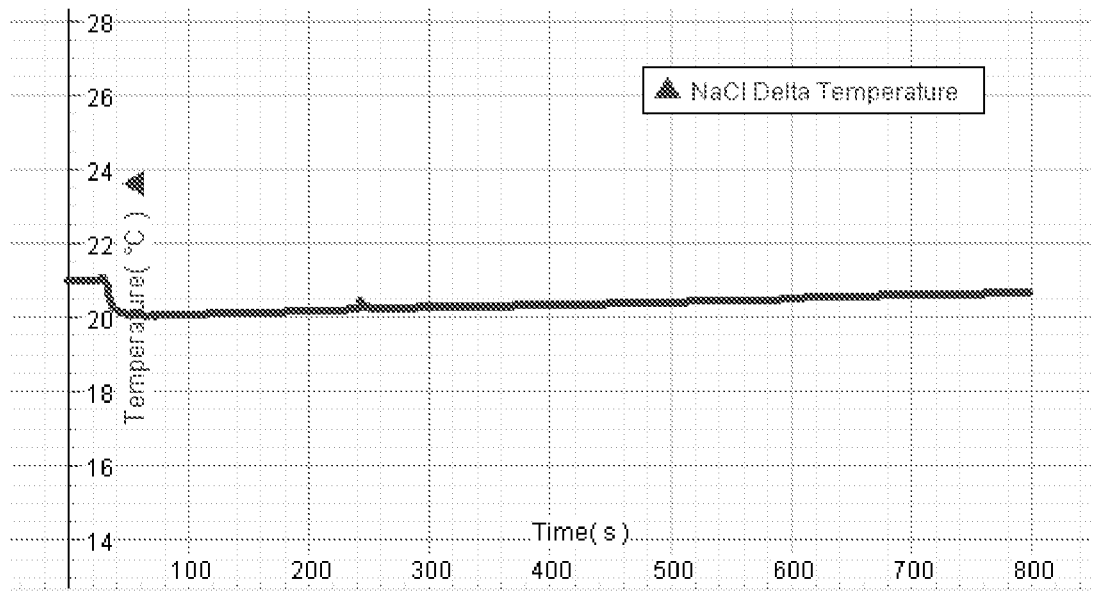
FIG. 10: Datastudio Temperature Profile for 1.37 M Sodium chloride in 100 ml of distilled water.
Figure 11:
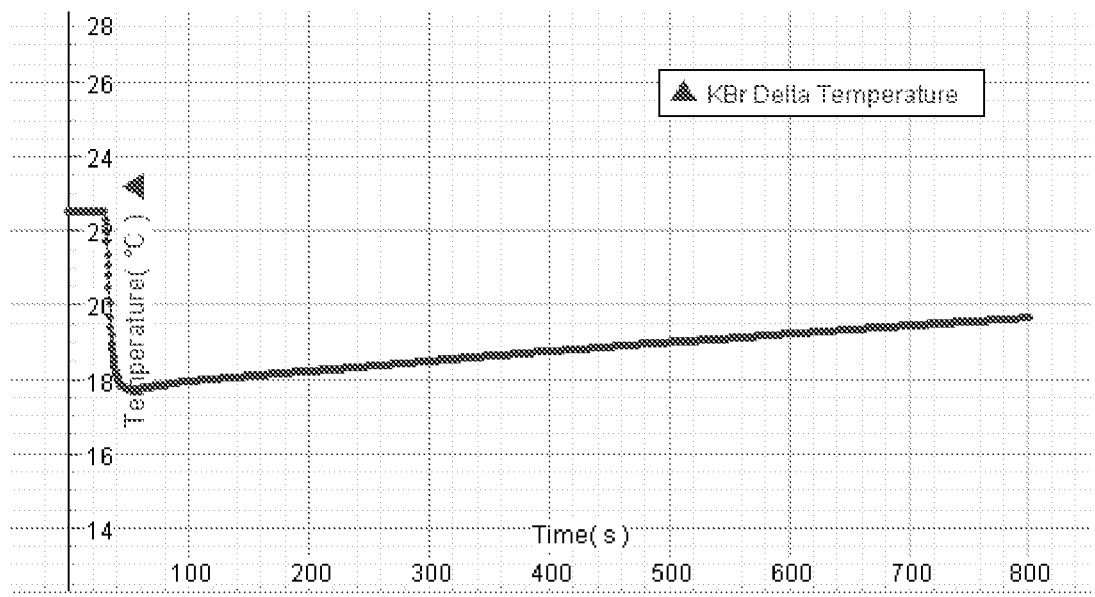
FIG. 11: DataStudio graph of temperature change associated with 1.37 M Potassium Bromide dissolution in 100 ml of distilled water.
Figure 12:
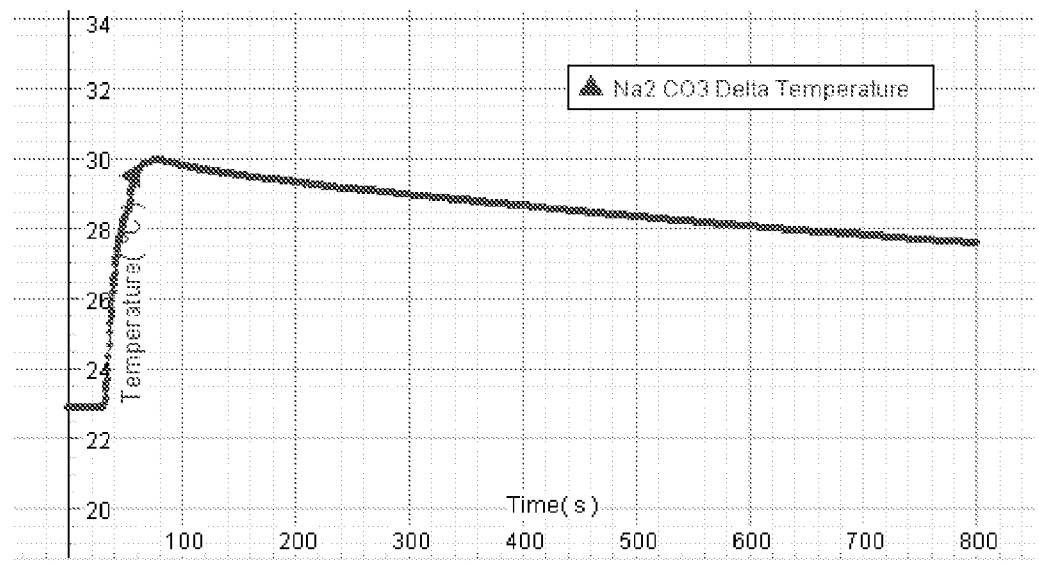
FIG. 12: Datastudio graph of temperature change associated with 1.37 M $Na_2CO_3$ dissolution in 100 ml of distilled water.

Each ionic salt demonstrated a unique endothermic or exothermic dissolution profile (FIGS. 10 to 12). In the case of potassium bromide and sodium carbonate significant temperature changes are apparent. These temperature changes achieve their maximum or minimum at the same time point as the corresponding Acoustic profile, demonstrating that the temperature change is driven in direct proportion to the dissolution of the solute. However, the elongated time taken to return to steady state for the temperature value is not reflected in the acoustic profile. This is clearly demonstrated in FIG. 6, where four methods of monitoring the dissolution profile, namely dissolved oxygen monitoring, colorimetric transmission spectroscopic determination, acoustic resonance and temperature profiling, were employed. It is apparent that the increase in dissolved oxygen, and decrease in temperature endpoints (c.a. 110 seconds) coincide with the acoustic profile reaching its minimum. Simultaneously the absorbance data reaches its maximum at this point. All data indicates dissolution being complete at this point. Therefore the increase in the acoustic profile (and those increases/decrease in the profiles of the other parameters) after this point must be due to some other parameters not directly associated with the dissolution process i.e. the reduction of the bubble layer in the case of the acoustic profile. As explained by Crawford, as the gas exits the solution the compressibility of the solution is reduced hence the speed of sound in solution increases again to its original level.

The dissolved oxygen experiment shows conclusively that gas is indeed being evolved from solution upon addition of a solute, and points to this being the main cause of the acoustic phenomenon. Further gas studies were carried out, where the distilled water medium was saturated with various gasses, namely nitrogen and argon, to show the effect of the gas expulsion when the available saturated gas differed from ambient air. These showed markedly different acoustic profiles when a standard sodium chloride dissolution was carried out, showing yet again the reliance of the acoustic effect on the nature of the gas in solution.

The dissolved gas investigations offer further options for varying the information obtainable from this technique. It is also possible that naturally occurring levels of gases in solution, in naturally occurring ratios, are expelled from solution at different rates, yielding more distinctive profiles, although this requires further study. This provides intriguing possibilities for manipulating the environment in which dissolution data is obtained.

The effect of mass of solute was explored by comparing identical masses of different Ionic salts. This was carried out to eliminate the possibility of additional mass being the driving force behind the frequency changes occurring in the glass vessel, as working on the basis of concentration alone would inherently yield different masses being dissolved during experiments. Concentration data will also be discussed.

Working around the 1.37 M value for sodium chloride (8 g) two 2 g-intervals below this value were studied for sodium chloride (NaCl), potassium bromide (KBr) and sodium carbonate ($Na_2CO_3$). It is demonstrated that no direct relationship exists between the dissolution of similar masses of different compounds, and it is quite clear that the concentration of the solute is instead a factor in eliciting an acoustic resonance profile. This is most clearly seen in the profile of potassium bromide. Although the concentrations corresponding to the masses of 4 g, 6 g and 8 g are too low to elicit a discernable downward dissolution driven portion of the curve, all 3 masses demonstrate a similar timescale required to return to steady state as the sodium chloride profiles, perhaps suggestive of a proportional rate of relaxation, i.e. a constant rate of micro-bubble evacuation from solution, though this requires further elucidation.

Figure 13:
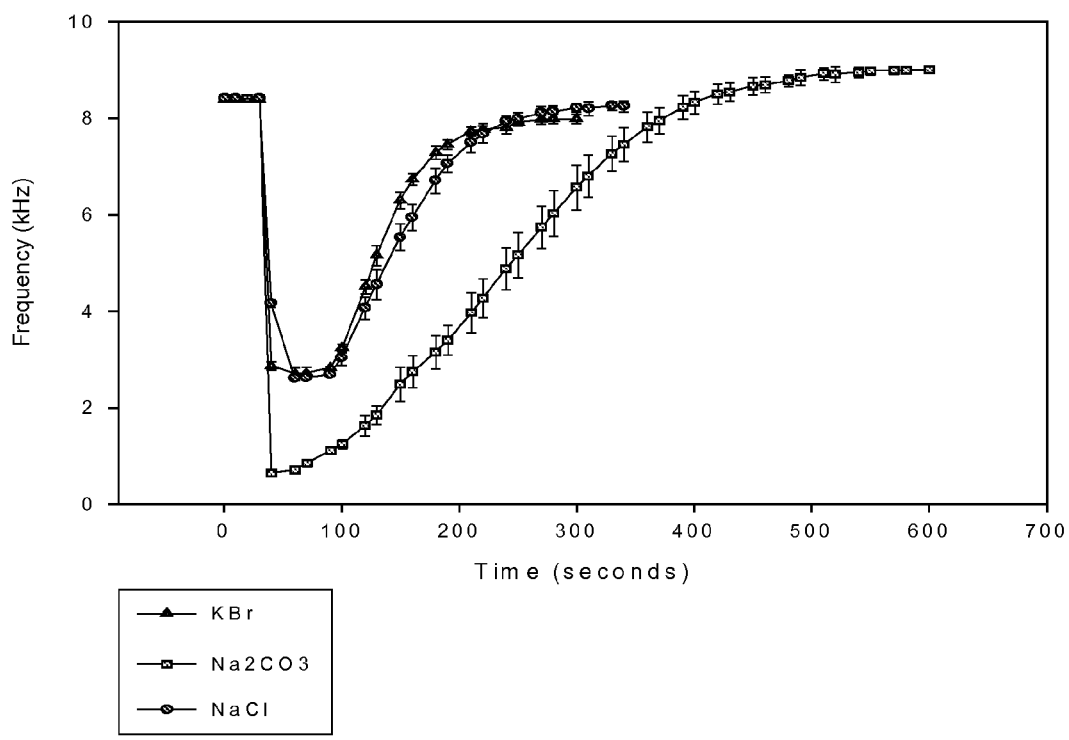
FIG. 13: Acoustic profile-comparison of the three ionic salts, Sodium chloride, Potassium Bromide and Sodium Carbonate. Each is distinctly identifiable from their unique profile.

Qualitative Capabilities of Acoustic Resonance Spectroscopy
Qualitative Compound Identification Results The various compound specific profiles of the three ionic salts sodium chloride, potassium bromide and sodium carbonate are displayed in comparison to each other in FIG. 13. An important characteristic of the acoustic profile is the frequency minima, particularly the downward dissolution driven portion of the curve, which is an analytically distinctive portion of the curve.

Figure 14:
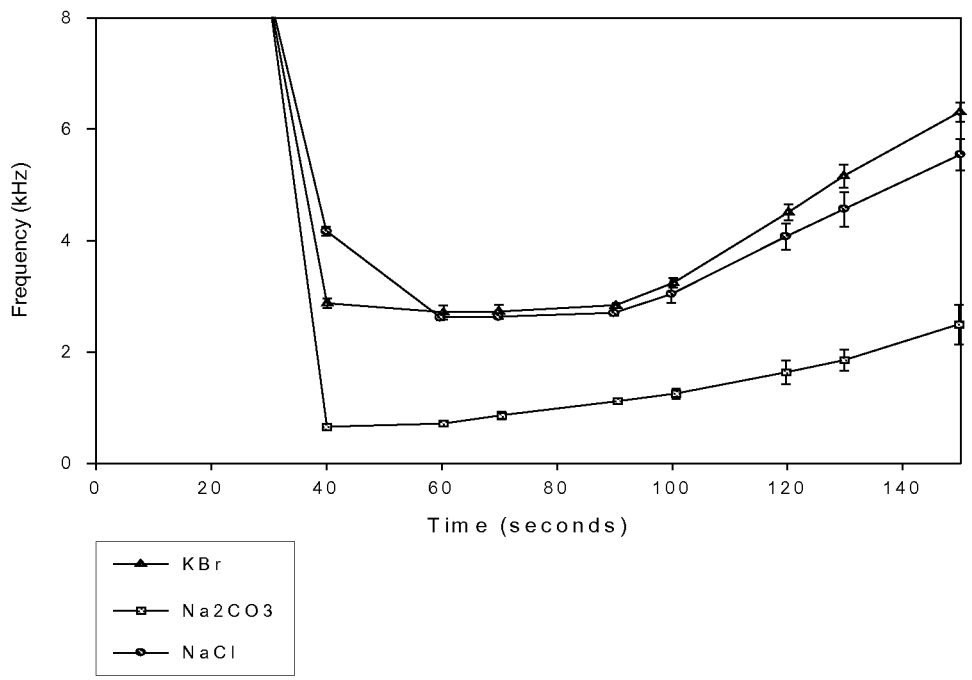
FIG. 14: Acoustic profiles of the three ionic salts, Sodium chloride, Potassium Bromide and Sodium Carbonate, a scaled up plot of the frequency well portion of the profile. Note the distinctly different primary detection point of each profile.

FIG. 14 focuses on the frequency minima of the spectrum for all three salts, highlighting the distinct differences between these compounds.

It can be seen from the distinct profiles, each compound is uniquely identifiable, and this holds true for a range of concentrations of each salt.

Crossover Analysis Results

The frequency band crossover method, utilizes all the data that is within the acoustic dissolution spectrum of a given compound, both the fundamental frequency profile, and all subsequent overtone profiles. These cross each other at various points in the spectrum and are unique to a specific compound and are variable with concentration.

Figure 15:
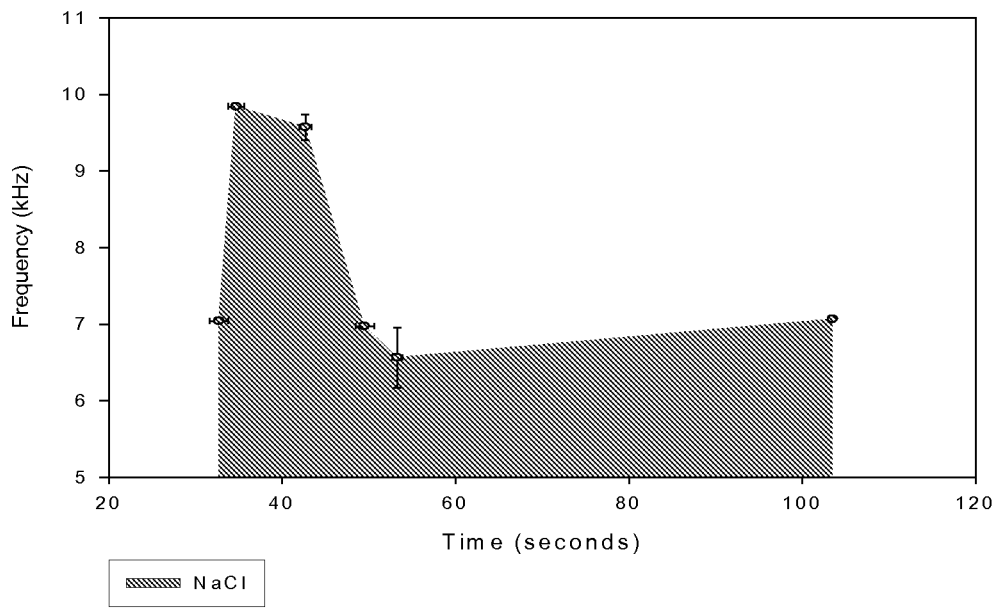
FIG. 15: Unique Crossover Points of Sodium chloride taken from Acoustic Spectra repeated in triplicate. Crossover analysis of Sodium chloride at 1.37 M concentration.

FIG. 15 shows the crossover pattern for sodium chloride at 1.37 M in 100 ml of double distilled water. As can be seen from this plot, the data points are quite stable, with just one of the points being variable, and only along the frequency axis.

Figure 16:
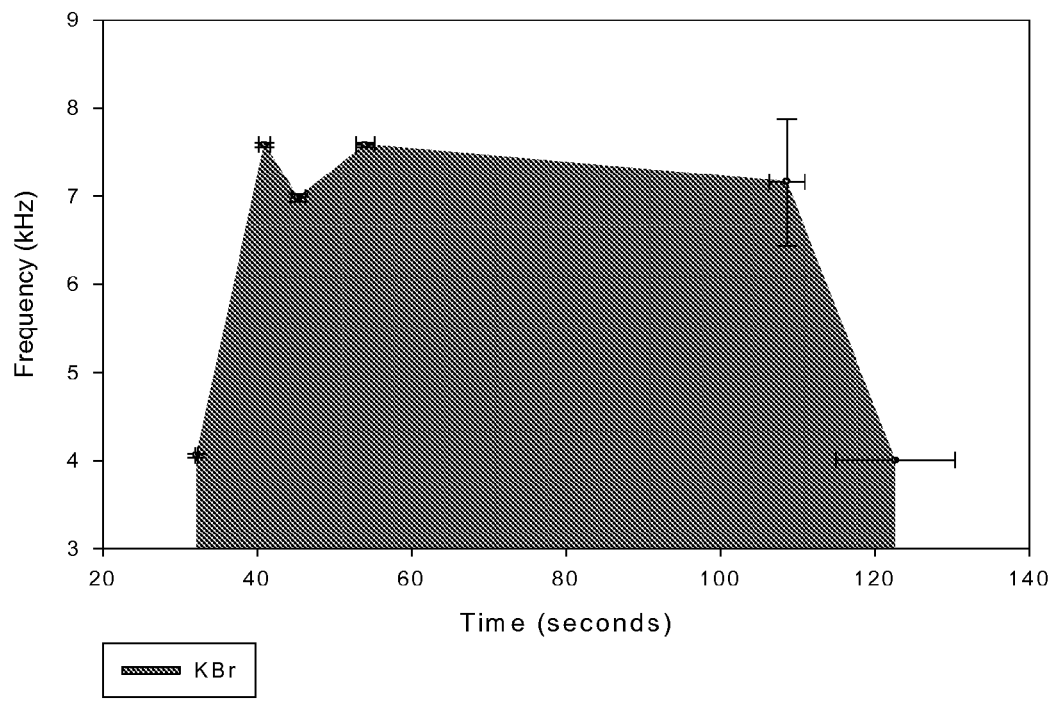
FIG. 16: Crossover analysis of Potassium Bromide at 1.37 M concentration in 100 ml of double distilled water.
Figure 17:
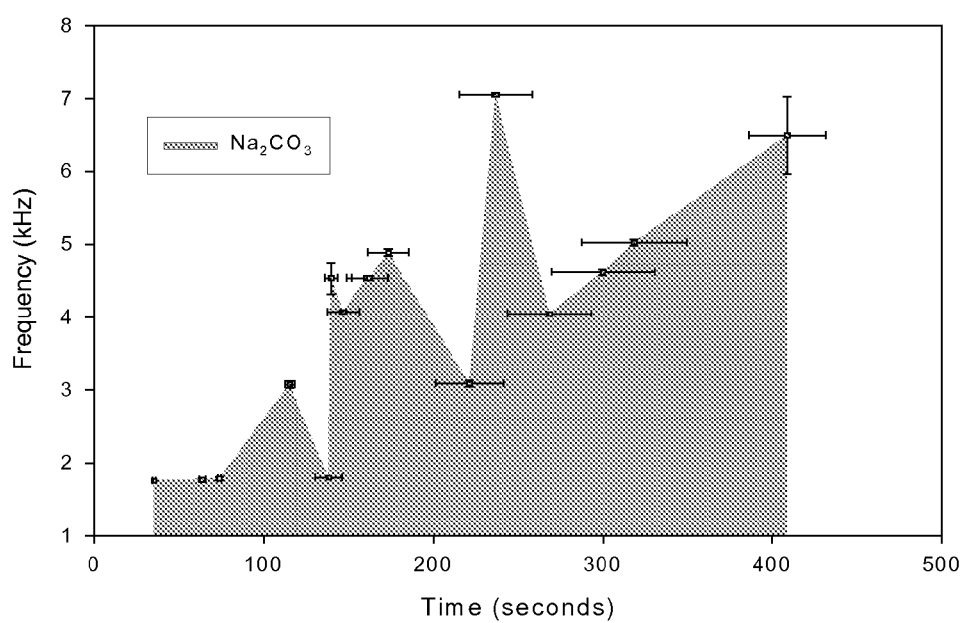
FIG. 17: Crossover analysis of Sodium Carbonate at 1.37 M concentration in 100 ml of double distilled water. Due to the greater complexity of Sodium Carbonate's Dissolution spectrum as opposed to the other ionic salts studied, there is a greater number of crossover points observed.

FIG. 16 shows the crossover pattern for potassium bromide at 1.37 M in 100 ml of double distilled water. The 2 later data points show an increased variability than was present in sodium chloride FIG. 17 shows the crossover pattern for sodium carbonate at 1.37 M in 100 ml of double distilled water. The level of complexity in the raw spectrum of sodium carbonate, not present in the spectra of the other two salts, gives rise to a greater number of crossover points. However the majority of these lie along the relaxation portion of the various frequency curves, giving rise to increased variability in these data points.

Figure 18:
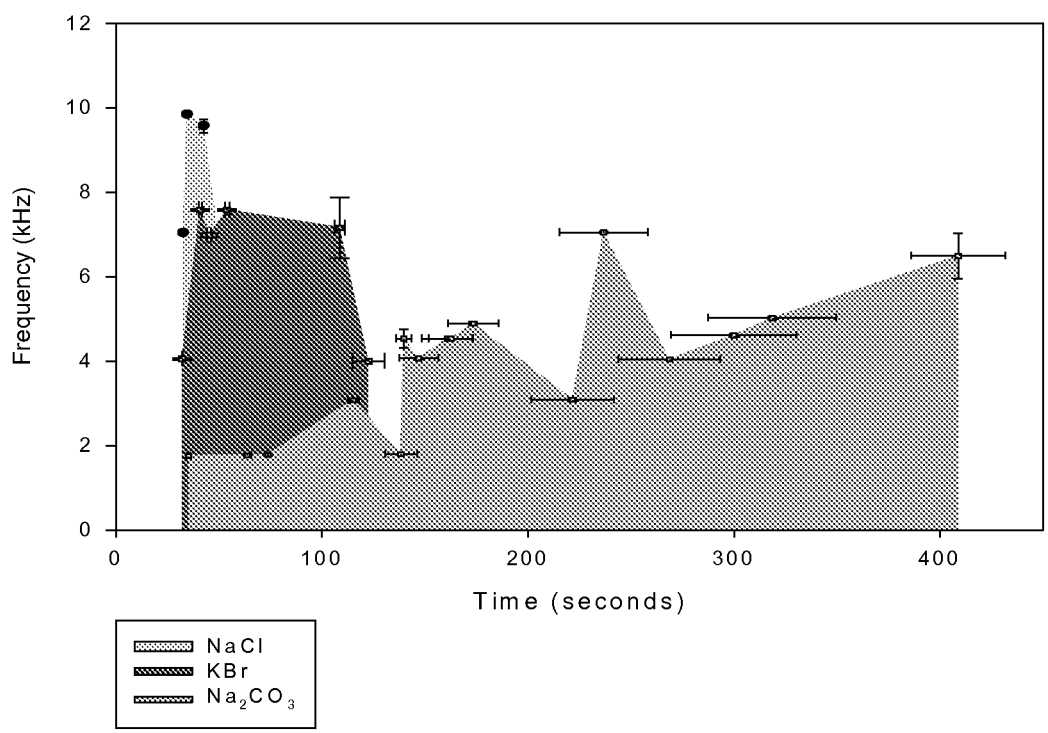
FIG. 18: Crossover Analysis Comparison for the three ionic salts. Note differing timescales and frequency positions of the data points for each salt.

FIG. 18 shows the comparison of the three salts crossover patterns; the overlap for these compounds is minimal, with each salt showing distinctly different crossover positions on both the frequency and time axes. This is further highlighted in FIG. 19 where the shaded portion of the Sodium chloride crossover profile has been removed to show the unique differences at the most reliable portion of the curves in question.

Figure 29:
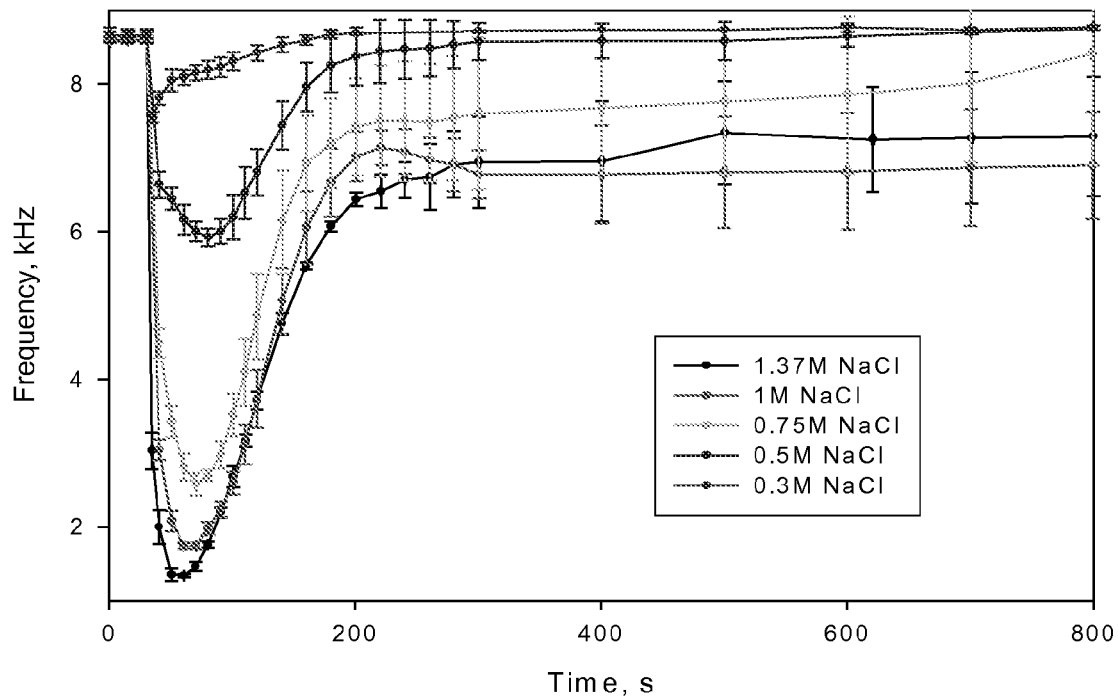
FIG. 29: Comparison plot of 1.37, 1, 0.75, 0.5 and 0.3M NaCl in 100 mls $dH_2O$.
Figure 30:
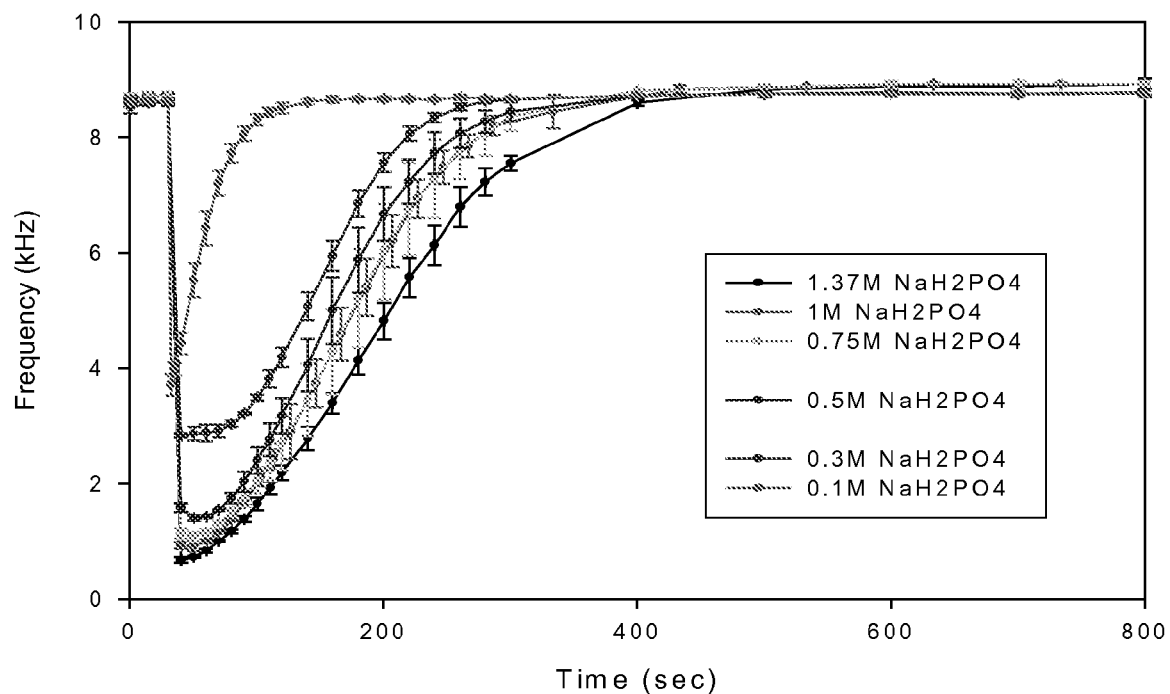
FIG. 30: Comparison Graph of 1.37 M, 1M, 0.75M, 0.5M, 0.3M, and 0.1M $NaH_2PO_4$ in 100 mls $dH_2O$.
Figure 31:
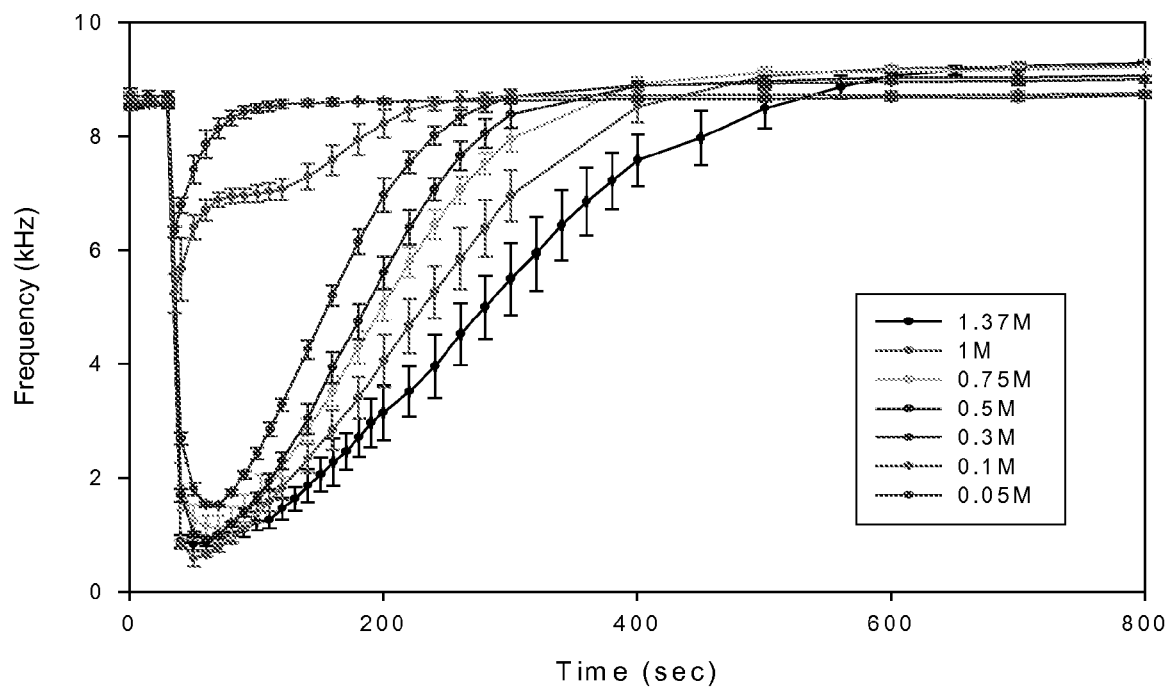
FIG. 31: Comparison Plot of 1.37, 1, 0.75, 0.5, 0.3, 0.1, and 0.05M $Na_2CO_3$ in 100 mls $dH_2O$.
Figure 32:
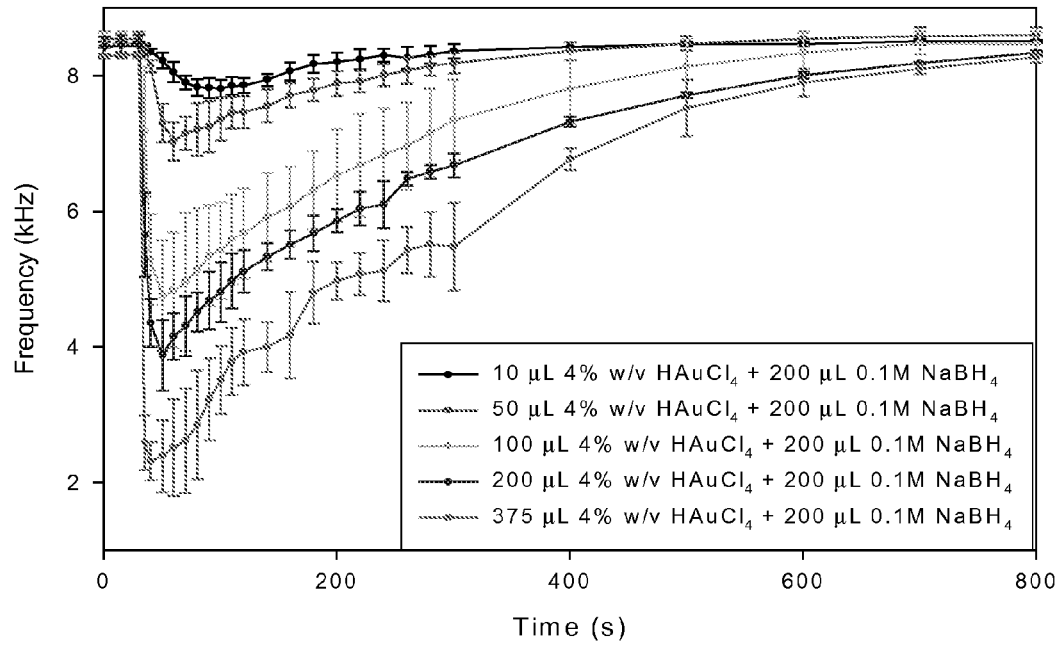
FIG. 32: Comparison of acoustic spectra used in reaction monitoring of the formation of gold nanoparticles, using different concentrations of gold salt and constant concentration of borohydride, each performed in triplicate in 100 mls of $dH_2O$. Note the intensity of the spectra increase with increasing formation of gold nanoparticles.
Figure 33:
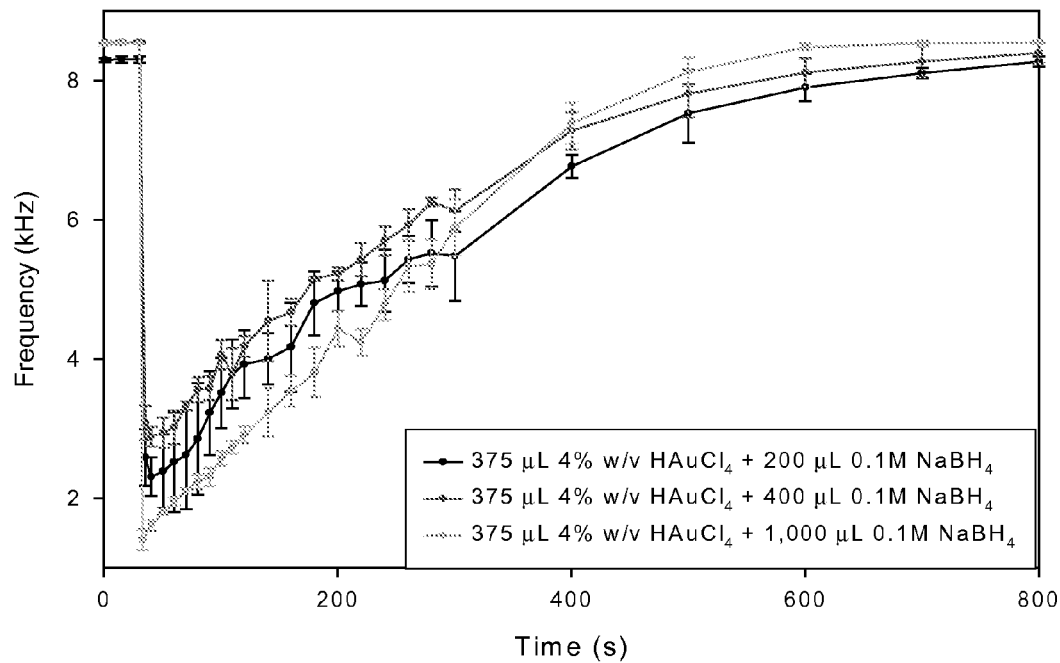
FIG. 33: Comparison of acoustic spectra of the formation of gold nanoparticles, using different concentration of borohydride, each performed in triplicate in 100 mls $dH_2O$.
Figure 34:
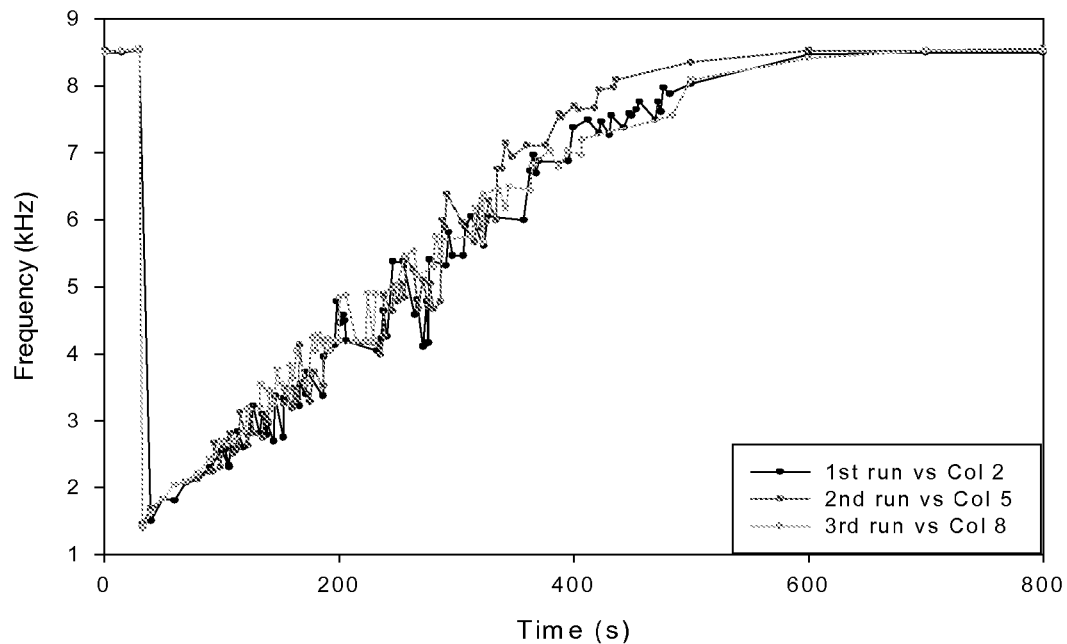
FIG. 34: Comparison of detailed peak of gold formation using 1 ml of 0.1 M $NaBH_4$ and 375 μL 4% $HAuCl_4$.
Figure 35:
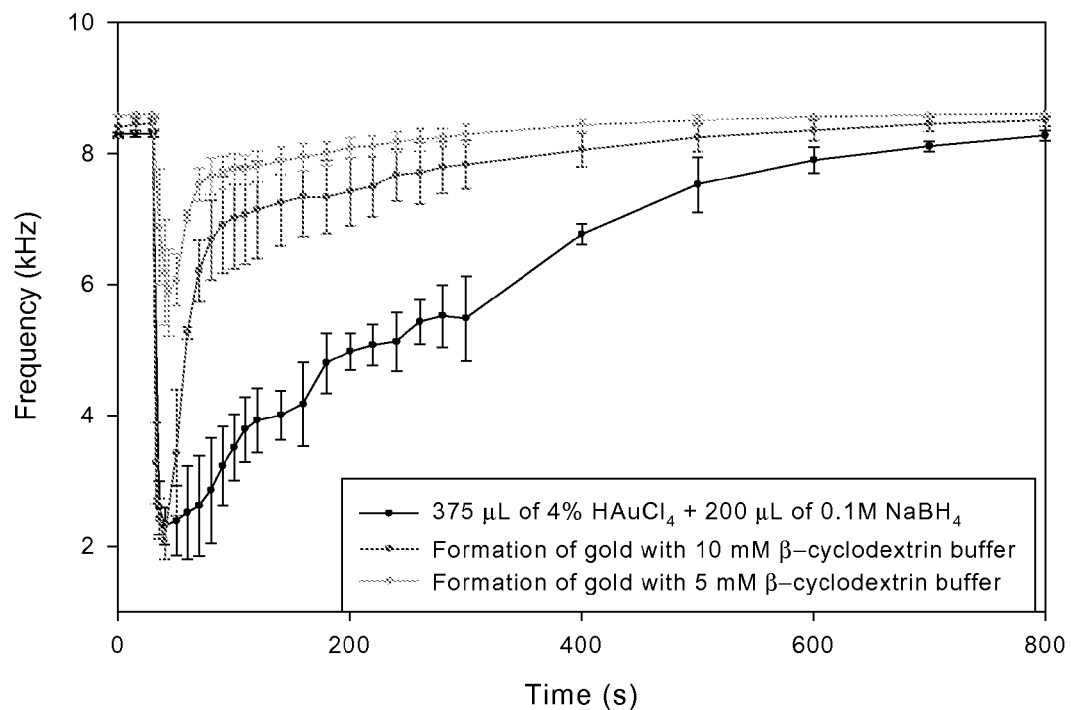
FIG. 35: Comparison of acoustic spectra of reduction of $HAuCl_4$ by $NaBH_4$, in presence or absence of β-cyclodextrin buffer, all spectra averaged from triplicate runs done in 100 mls $dH_2O$. Results indicate that in the presence of cyclodextrin, the formed gold nanoparticle size is controlled by the size of the cyclodextrin present.
Figure 36:
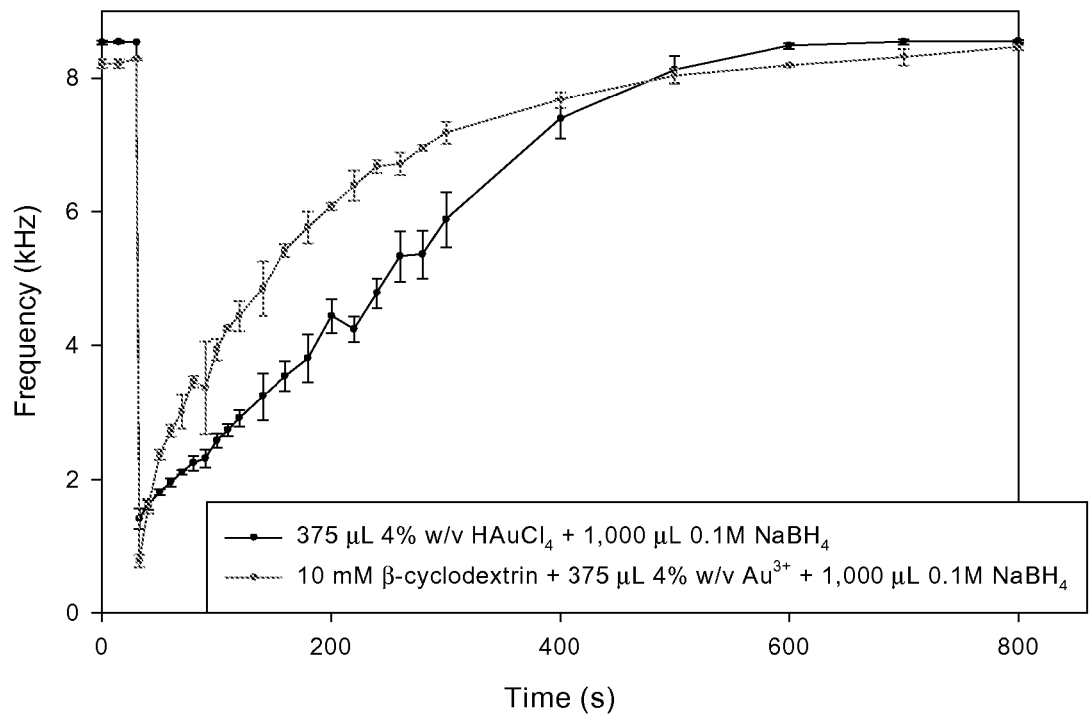
FIG. 36: Comparison of acoustic spectra for the formation of colloidal gold, comparing the presence and absence of β-cyclodextrin, experiments performed in triplicate, each in 100 mls of deionised water.
Figure 37:
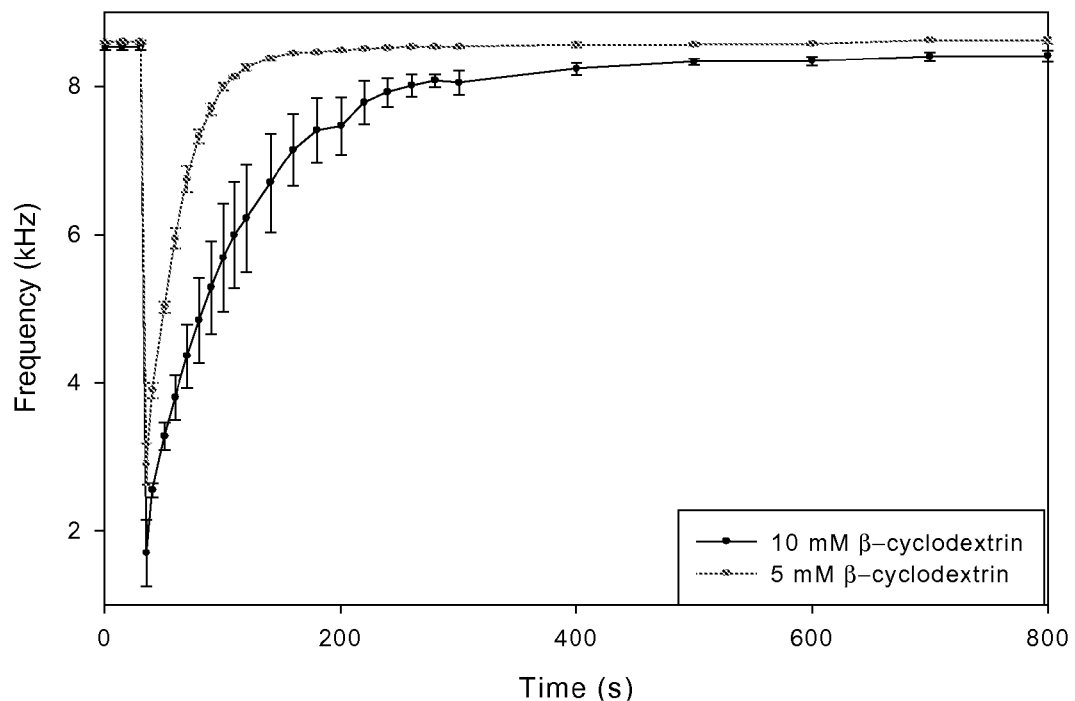
FIG. 37: Comparison of acoustic spectra of β-cyclodextrin, run at 5 mM and 10 mM in triplicate in 100 mls $dH_2O$.
Figure 38:
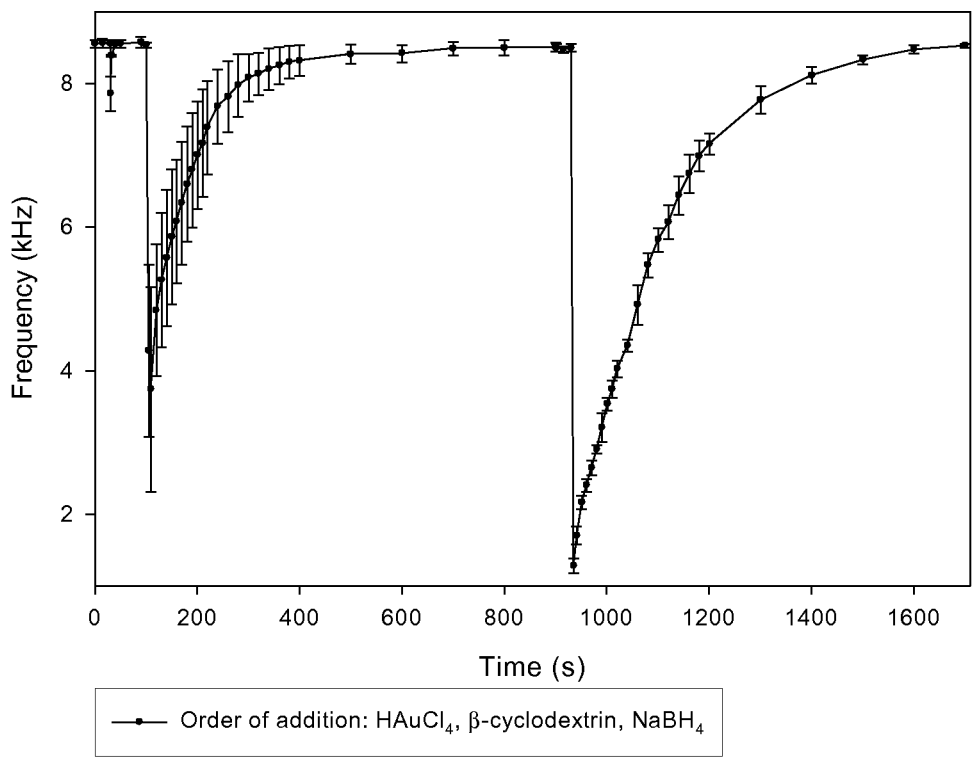
FIG. 38: Spectrum of gold nanoparticle formation using 375 μL 4% w/v $HAuCl_4$, 10 mM β-cyclodextrin and 1,000 μL 0.1 M $NaBH_4$, performed in triplicate in 100 mls $dH_2O$. Indicates the usefulness of the technique in reaction monitoring applications. In the absence of cyclodextrin, no response in observed. The later profile indicates the reaction with borohydric acid resulting in the formation of the gold nanoparticles. It should be noted that there is no acoustic response for sodium borohydride in the absence of gold chloride and vice versa. This indicate the profiles are purely as a result of a reaction taking place. Furthermore, effects are observable at microliter quantities. Cyclodextrin is used to control the nanoparticle size.
Figure 39:
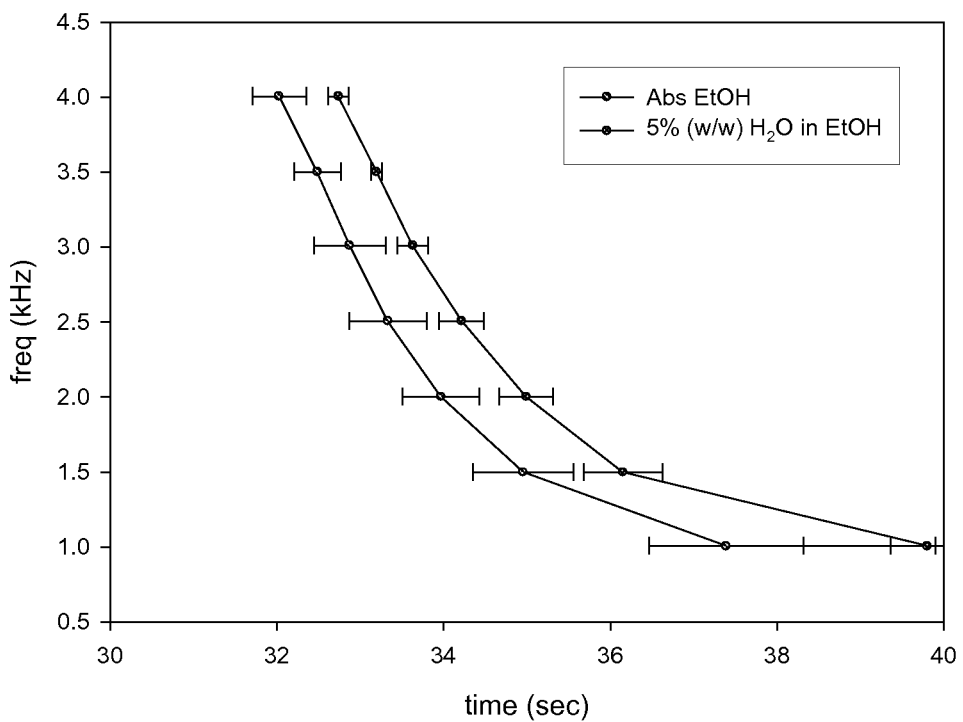
FIG. 39: Comparison of acoustic spectra of $H_2O$ content in absolute ethanol and in 5% EtOH (w/w). The results indicate that the technique is sensitive enough to clearly differentiate between solutions of absolute and ethanol containing water at a concentration of 5% w/w of $H_2O$.
Figure 40:
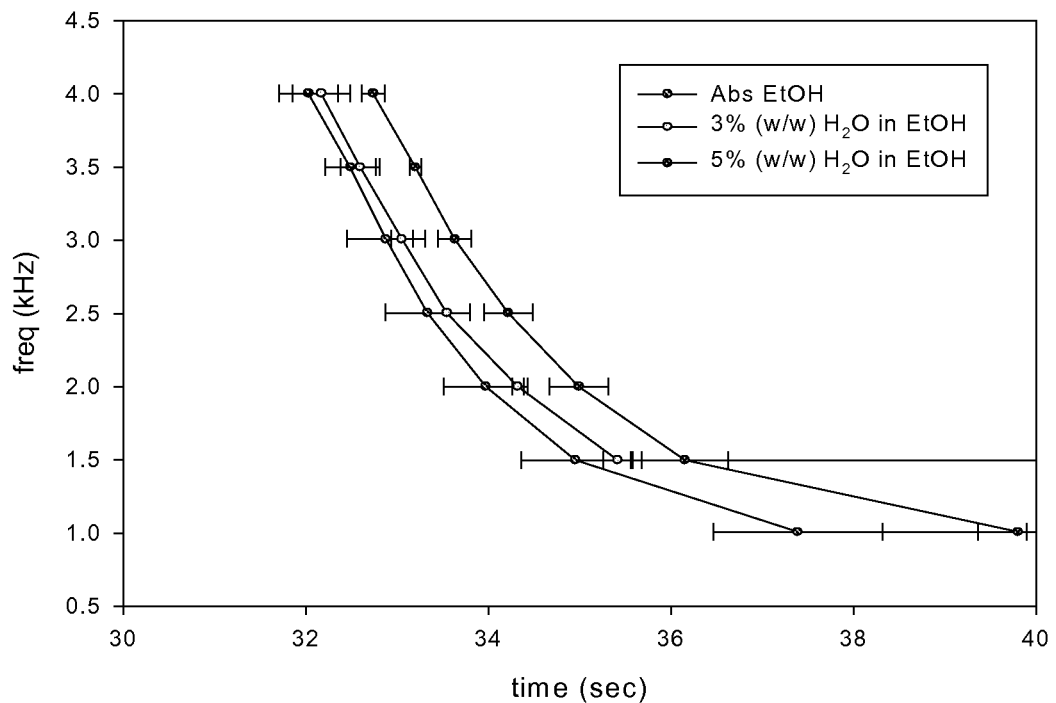
FIG. 40: Comparison of acoustic spectra of $H_2O$ content in absolute ethanol, in 3% EtOH (w/w) and in 5% EtOH (w/w).
Figure 41:
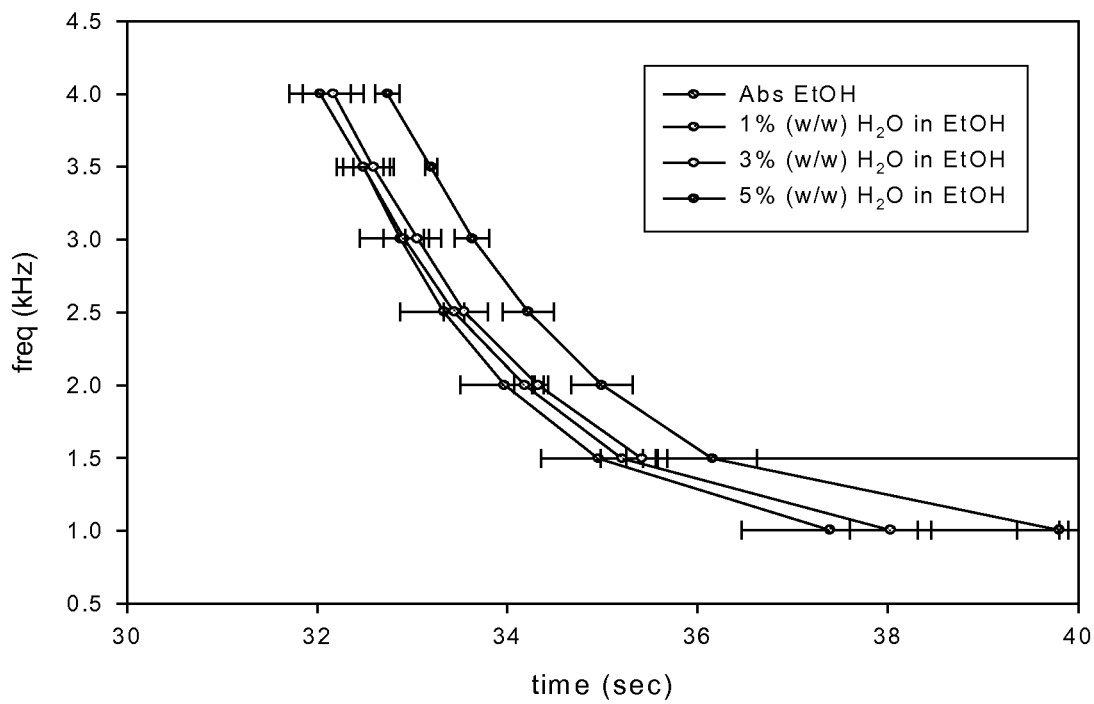
FIG. 41: Comparison of acoustic spectra of $H_2O$ content in absolute ethanol, in 1% EtOH (w/w), in 3% EtOH (w/w) and in 5% EtOH (w/w). The results indicate that the technique is sensitive enough to clearly differentiate between solutions of absolute and ethanol containing water at even concentrations of 0, 1%, 3 & and 5% w/w of $H_2O$. This means the moisture content of solvents can be estimated e.g. by adding acetonitrile to water will illicit an acoustic spectrum which varies with the moisture content of CAN.
Figure 42:
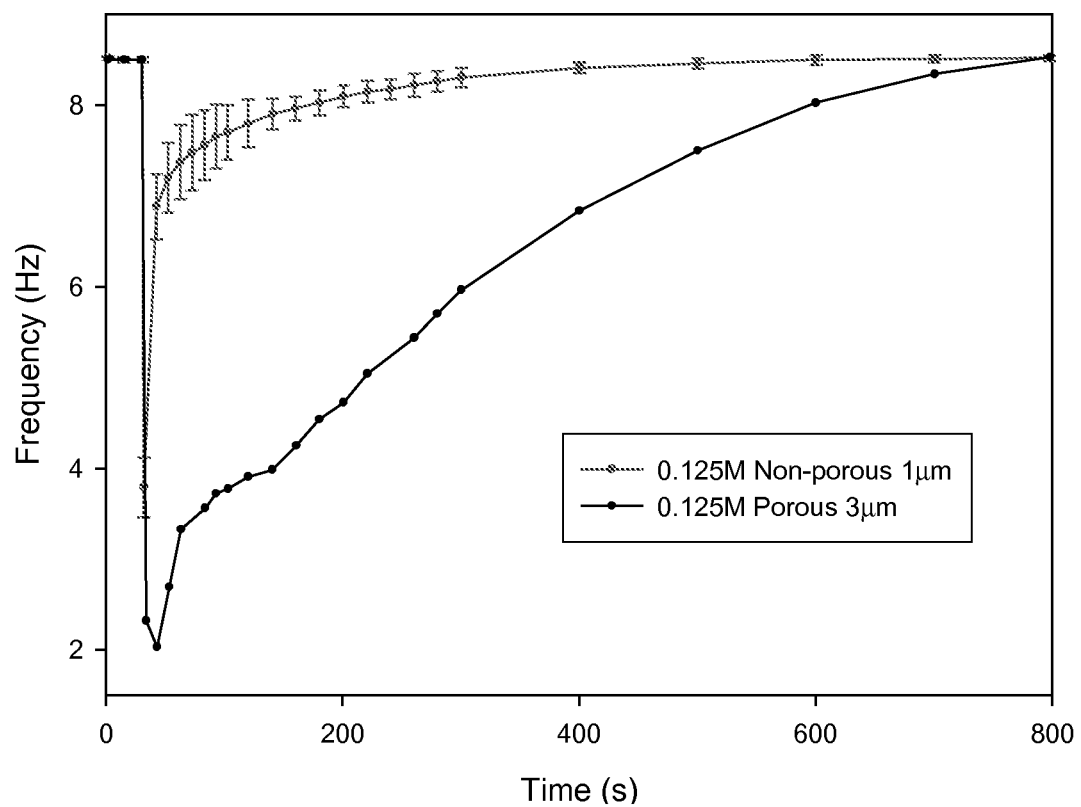
FIG. 42: Comparison of 0.125 M $SiO_2$ samples in 100 mls $H_2O$. These results indicate that the technique is capable of distinguishing between particles of varying porosity.

Concentration data is provided in FIGS. 29-31, which illustrate the effect of measuring the spectra of different concentrations of three different compounds. The figures illustrate the formation of the minima with increasing concentration. The lowest concentration shows an instantaneous dissolution. As the concentration increases a distinct minima appears. This may be due to an increased number of nucleation points for gas bubbles to form due to the presence of surface area on the un-dissolved material. The deflection in the minima is not linear with the increase in concentration. It is possible to differentiate between all concentrations. All three compounds reach their lowest minima below 2 KHz which may indicate there is a finite amount of gas which is expelled during each dissolution event. Sodium chloride returns to a different steady state with each concentration measured in comparison to the two other compounds due to moisture in the compound. Sodium dihydrogen phosphate has a similar return slope value for all concentrations whereas sodium carbonate has a different return slope value for all concentration measured. This may indicate that both compounds have a distinct mechanism for the liberation of gas. Sodium carbonate would appear to yield different size bubbles with different concentration and sodium dihydrogen phosphate does not.

Discussion

The qualitative and the quantitative capabilities of the acoustic resonance system described earlier, are clearly demonstrated through both the use of the fundamental frequency profile for each compound (e.g. as shown in FIG. 13) and through the use of the crossover point method, which gives a unique fingerprint for each compound. A fingerprint library can then be provided through accumulation of standard spectra.

Looking closely at the downward curve of the frequency minima in FIG. 14 there is a distinction between the minima of each of the three salts, Sodium chloride, potassium bromide and sodium carbonate, indicating a different dissolution rate for each salt. It is quite likely that kinetic data for the dissolution process is directly discernable from the dissolution spectrum of an individual compound; this requires further investigation. It is likely that an individual compounds rate of uptake into solution plays a direct role in the distinctive shape of the compound's acoustic profile.

Figure 19:
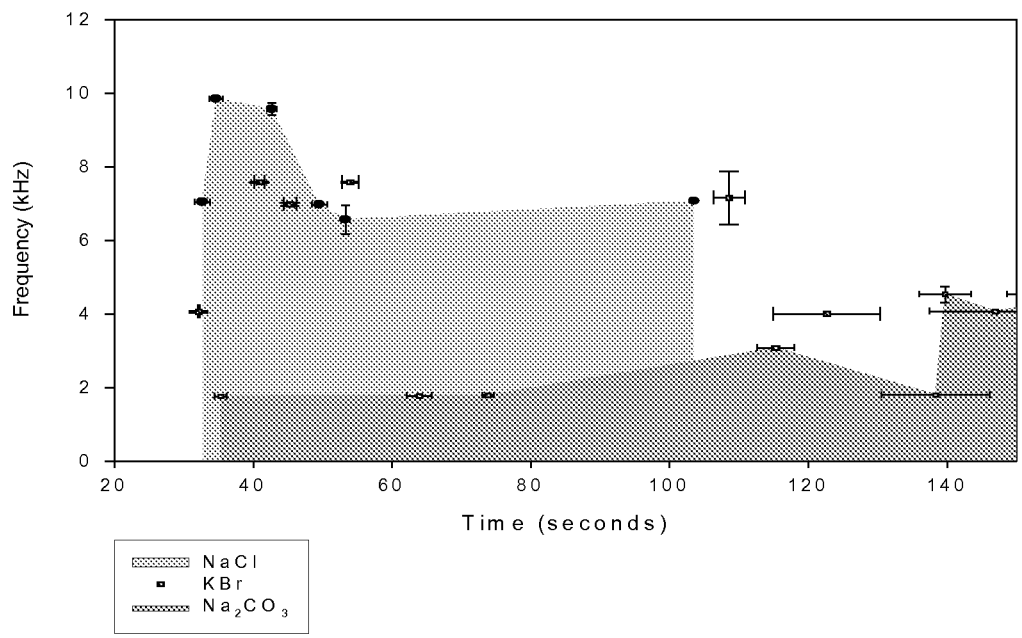
FIG. 19: Crossover Analysis Comparison of the three ionic salts. This plot is restricted to the more reliable area between 30 and 120 seconds. (The shading for Potassium Bromide has been removed to illustrate the number of identity supporting data points available for each salt). Note that each salt has at least 4 reliable data points available for sufficient fingerprint identification.

The crossover analysis method is likely to be even more reliable in terms of compound identification, as it utilizes more unique markers within the dissolution spectrum of a compound than the fundamental curve alone. The crossover method utilizes the overtones and resonance bands within the spectrum, as well as the fundamental resonance bands, noting the frequency and time at which these bands intersect within the spectrum. These points are varied across the spectrum, with their positions becoming more variable as the timescale of the dissolution progresses. Once documented, these points yield a distinct fingerprint for a compound, which can be easily overlaid on other compound spectra for comparison (See FIG. 18). FIG. 19 focuses on the more reliable frequency minima portion of the spectra, which yields the most reliable data points for identification, with at least four data points for each salt being highly reliable and unique for identification. It is entirely possible to create a computer program that could accomplish this automatically, as opposed to the manual logging of points currently carried out.

Particle Sizing Capabilities of the Acoustic Resonance System

Particle sizing of active pharmaceuticals is of major concern for a variety of industries, both in terms of raw materials going into a reaction and the resulting products of such syntheses. The particle size of a compound affects its rate of dissolution; the pharmacokinetic uptake into the human body and it is also an important factor in regards to the stability of the active ingredient over time, and susceptibility to microbial degradation.

Particle sizing of compounds is currently monitored, in lab environments, through the use of expensive laser and light scattering technology such as Malvern™ and Lasentech™. BARDS offers a less expensive alternative.

Before particle sizing, the analytes is ground and passed through particle sized gradient sieves and shaken with an accompanying agitation device. The size of the fraction recovered for each particle size distribution varied with each individual grind. The recovered fractions are run immediately or stored in sealed containers to avoid the absorption of moisture.

Discussion

Figure 20:
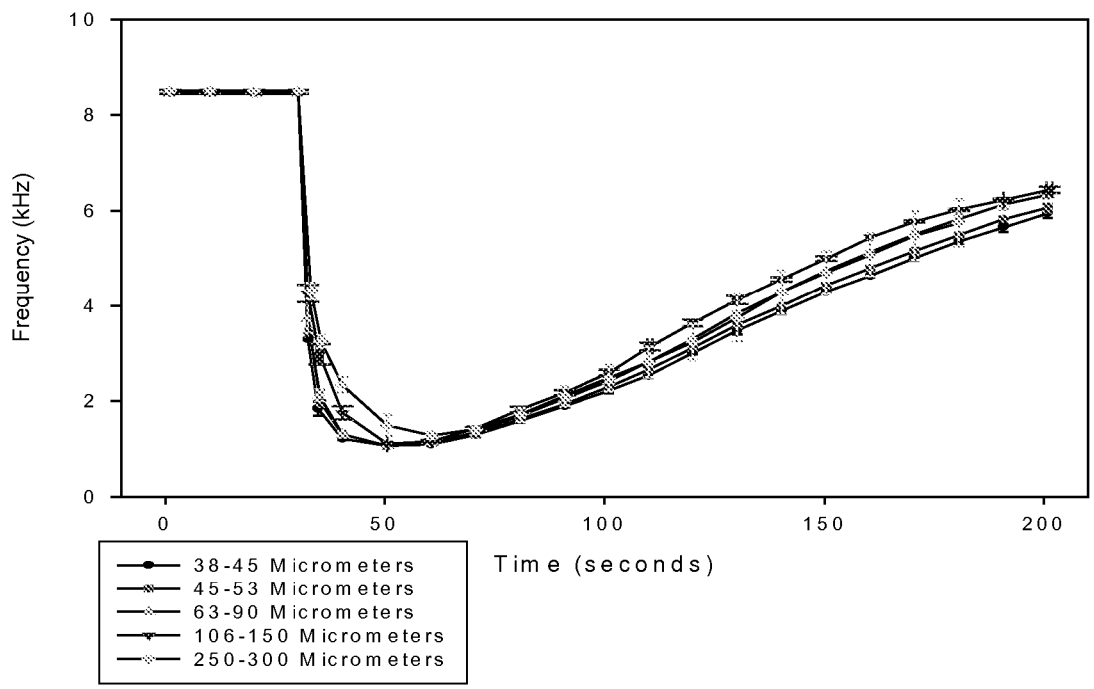
FIG. 20: Particles size distribution profile comparison. The five observed distribution bands are displayed in full. Note the increased depth of the frequency minima on the descending portion, with the reduction in particle size distribution.
Figure 21:
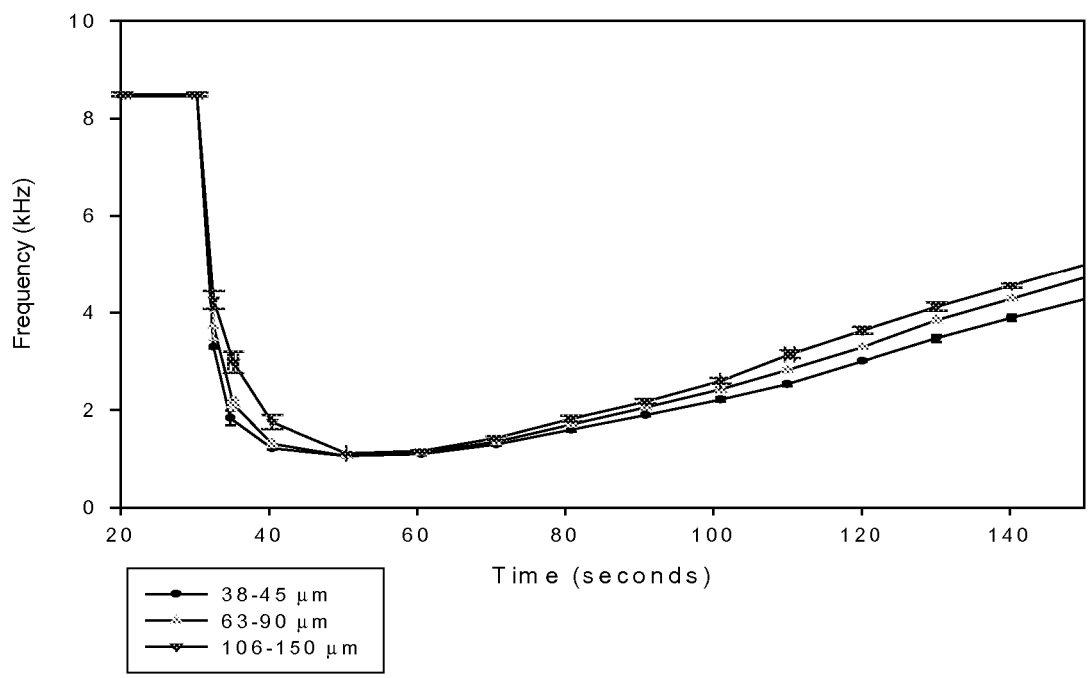
FIG. 21: Particle size distribution-comparison of Sodium Chloride. Note that best separation is achieved at the frequency minima portion of the profile.
Figure 22:
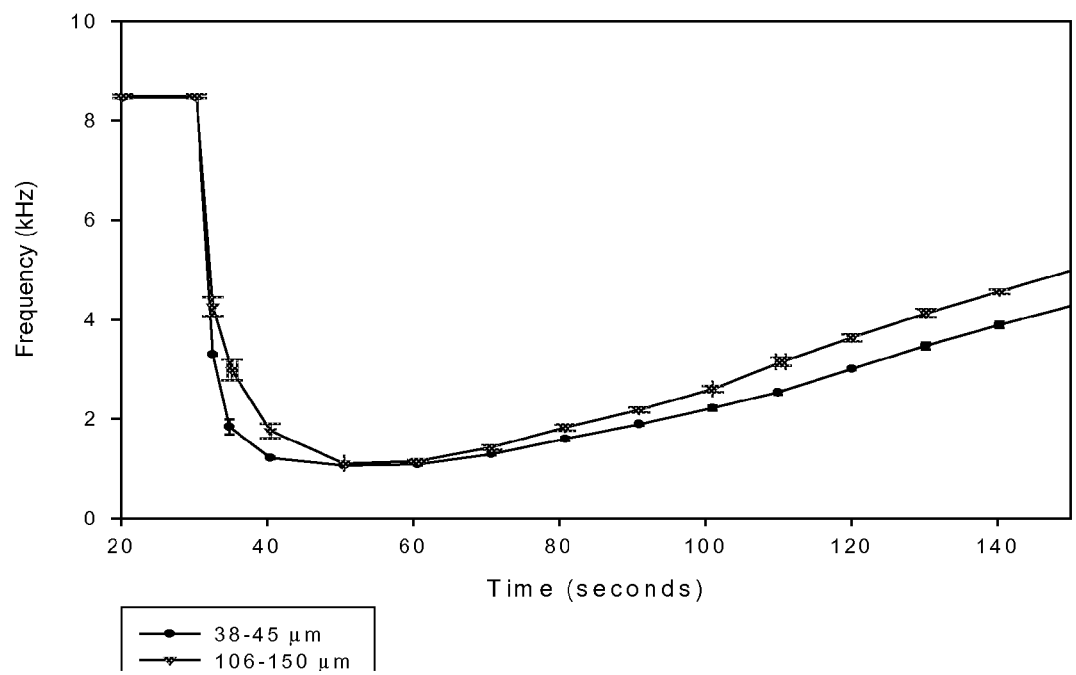
FIG. 22: Particle Size distribution profile comparison of Sodium Chloride with the 63-90 distribution removed.

The ability of the acoustic resonance system to differentiate between different particle sizes of the same compound is demonstrated in FIGS. 20 to 22 for sodium chloride. FIG. 20 shows the 5 particle size distributions utilized in the experiments, however the degree of separation between these distributions is not discernable at all time points. However, only one time point is required to make the differentiation. Also, the larger the distribution the greater the standard deviation which may be useful in determining distribution range. FIG. 22 shows the 38-45 μm and 106-150 μm particle size distributions, separation of distributions is apparent across the majority of the spectrum. As the particle size of the sample decreases, so too does the depth of the frequency minima. This may be due to the presence of a greater number of nucleation sites for the generation of micro-bubbles. The greater surface area due to the smaller particle size facilitates this process.

Sucrose was also examined in terms of particle size separation. The three larger particle size distributions, 106-150 μm, 180-250 μm and 300-355 μm, were examined (see FIGS. 23 and 24).

Figure 24:
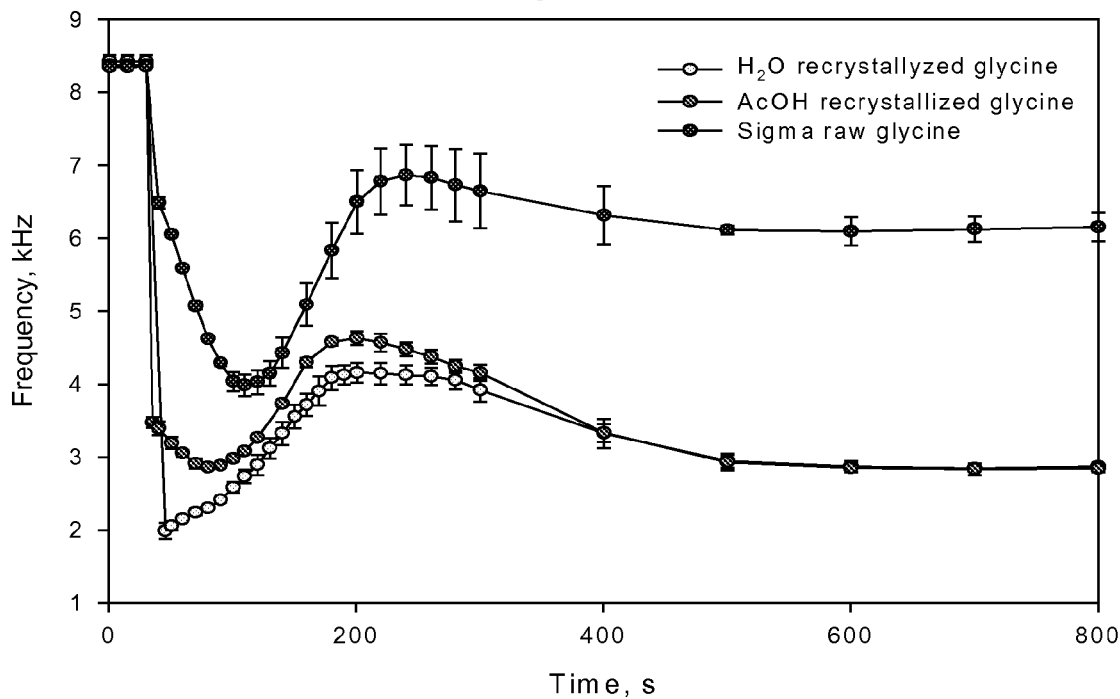
FIG. 24: Acoustic Profiles of Glycine and its α (water recrystallised) and γ (AcOH recrystallised) polymorphs.
Figure 25:
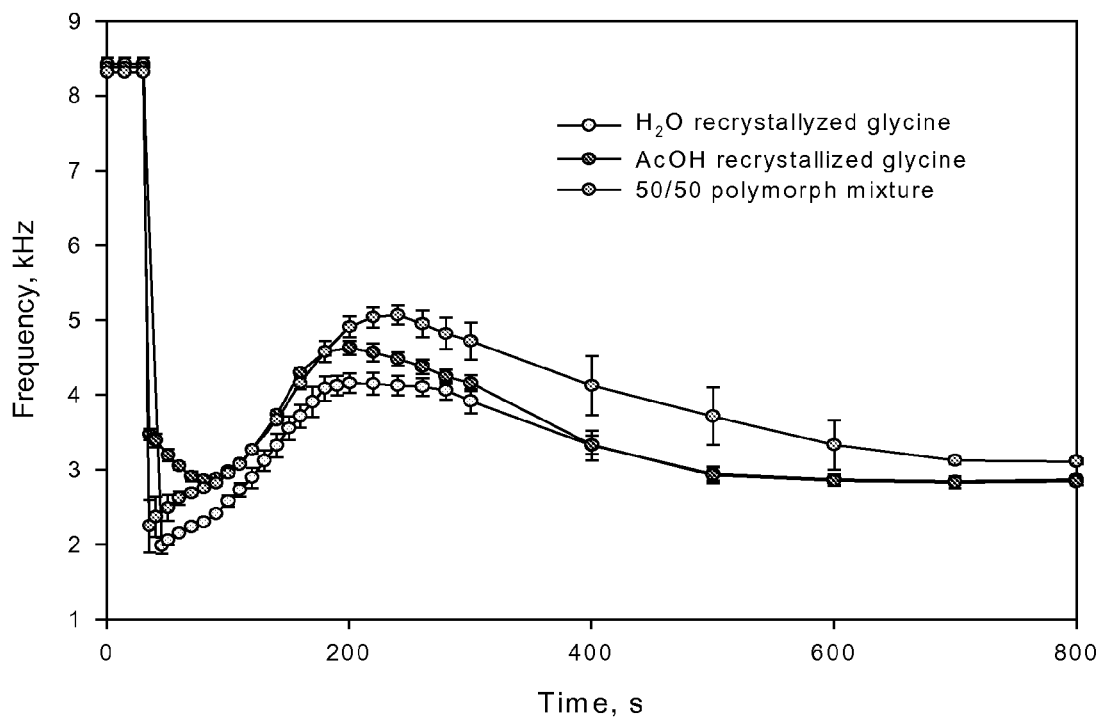
FIG. 25: 50:50 mix of two polymorphs of glycine.
Figure 26:
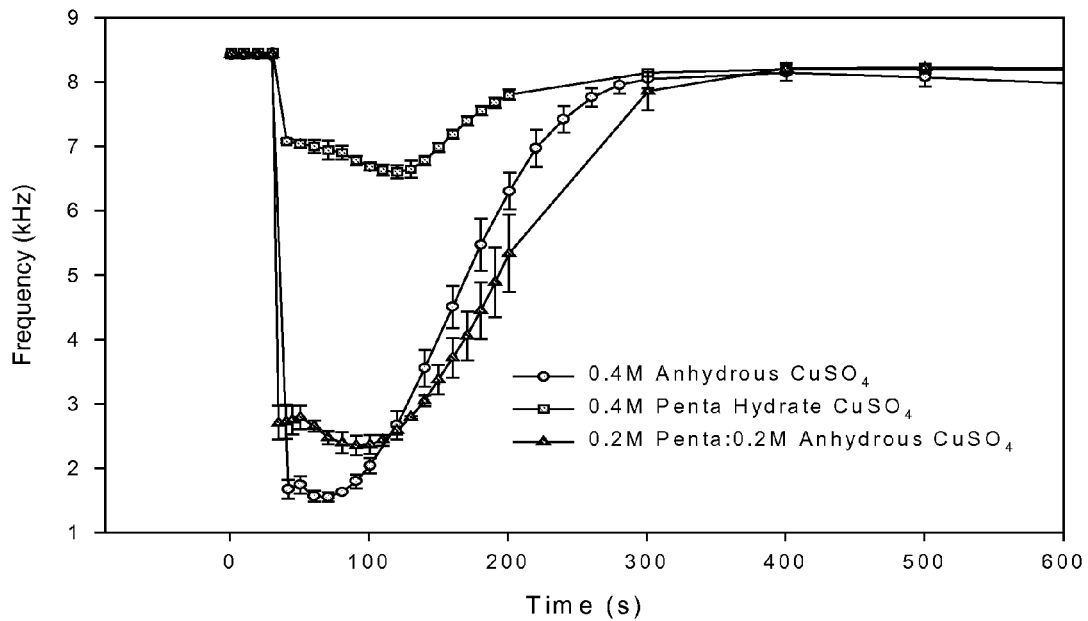
FIG. 26: Acoustic profiles of Copper Sulphate, Copper Sulphate pentahydrate and a 50:50 mixture of the two compounds.
Figure 27:
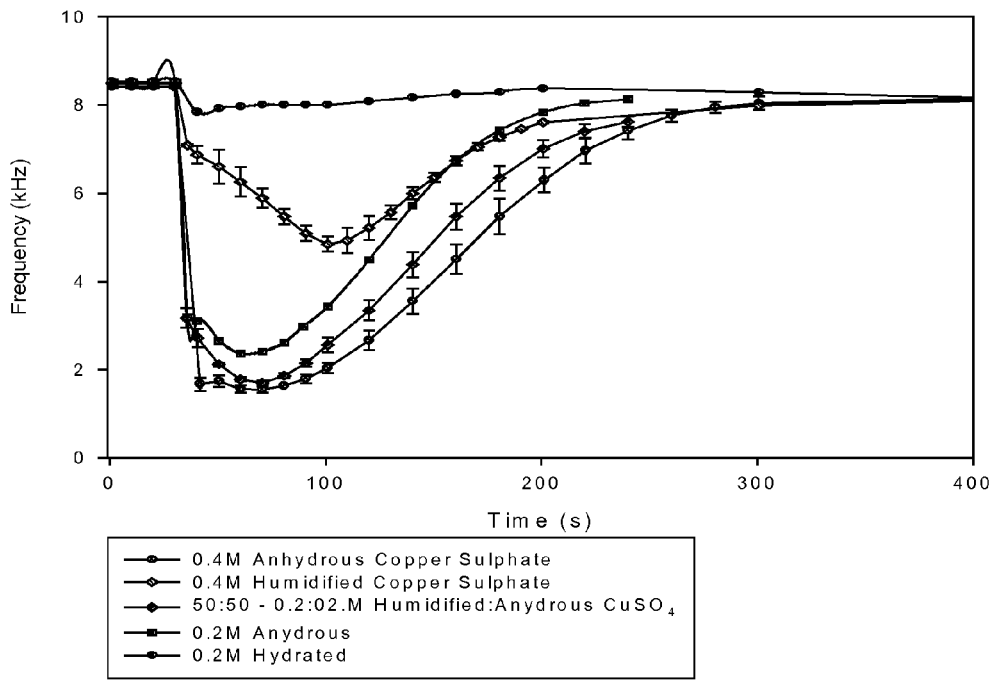
FIG. 27: Hydration effect comparison study on Copper Sulphate Pentahydrate and the anhydrous form. Note that the sum of the frequency change of both the 0.2M hydrated form and anhydrous form, matches that of the 50:50 mix of the two forms.
Figure 28:
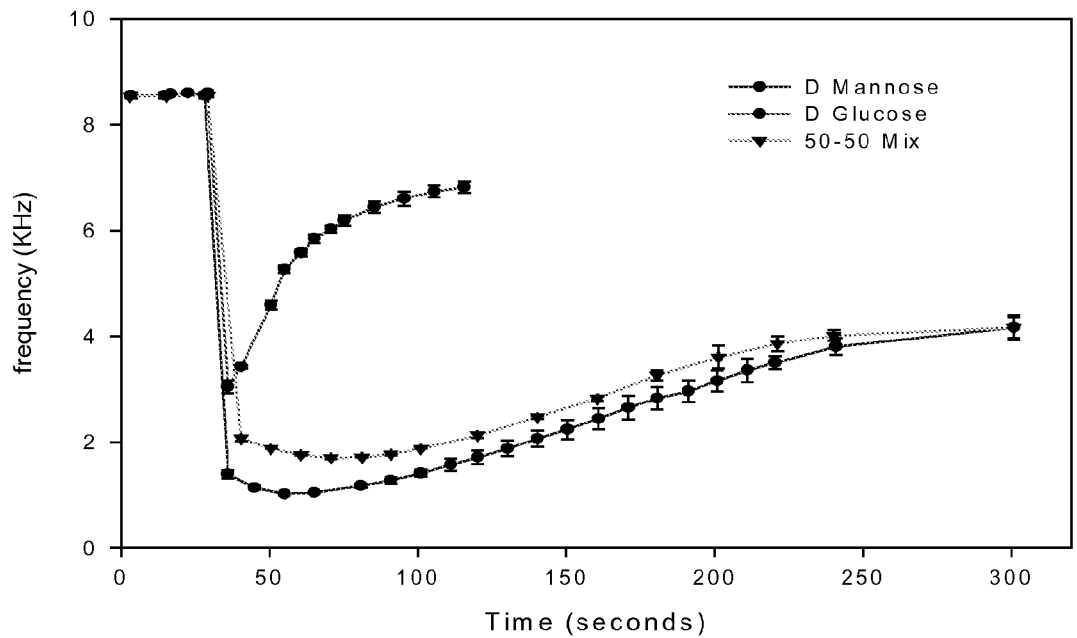
FIG. 28: Acoustic profiles of epimers—glucose and mannose. Also shown is the profile of a 50:50 mix of the two epimers.

FIG. 23 shows these three particle size distributions comparatively, and it is clear that these size distributions are separable both in terms of their unique profile shape and initial detection points. FIG. 24 removes the overlapping 106-150 μm profile, clearly demonstrating the degree of separation for the two larger distributions. Whilst the three distributions are clearly defined and separable, sucrose displayed the opposite trend to that of the sodium chloride. The smaller particle size distribution displayed the shallower frequency minima, with frequency minima depth decreasing with increasing particle size. It is possible that such trends exist solely within the particle size distribution dine of a particular compound.

Despite these conflicting trends, it is quite clear that particle size determination on the micrometer scale is entirely possible utilizing this technique. Nano-meter scale sample material is difficult and expensive to source at the current time, and equally difficult and expensive to prepare in house, meaning that the ability of the current apparatus to separate nano-scale particles is as yet undetermined. Undoubtedly as the refinement of this apparatus improves and progresses, these limitations will minimize significantly.

Acoustic Resonance Determination of Crystalline Polymorphs

Acoustic resonance spectroscopy has been found to have the ability to determine differences between different crystal polymorphs of the same compound, for example, glycine. Polymorphs are crystals of the same chemical compound, of the same molecular weight, which have different crystal structures and in some cases, different physical properties. These different crystalline structures are typically determined using light scattering and X-ray diffraction techniques, which are expensive equipment to purchase and maintain. The effectiveness of the acoustic resonance system at determining these crystalline differences is presented in FIG. 24.

Drug Loading of Porous Particles

The technique has also been found to be capable of monitoring drug loading of silica microparticles. The analysis is based on the porosity of the particles used, e.g. silica microparticles. When the pores are accommodate various amounts of drug, then different acoustic spectra are observed according to the porosity and the drug loading ability.

The words "comprises/comprising" and the words "having/including" when used herein with reference to the present invention are used to specify the presence of stated features, integers, steps or components but does not preclude the presence or addition of one or more other features, integers, steps, components or groups thereof. It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. The invention is not limited to the embodiments hereinbefore described but may be varied in both construction and detail.

REFERENCES

Crawford, F. S., Am. J. Phys. 50(5), 1982, "The Hot Chocolate Effect".

The invention claimed is:

1. A method of analysing a test material comprising the steps of:
   inducing a resonant acoustic emission from a vessel containing a solvent and measuring said resonant acoustic emission, said vessel being made of a resonant material, wherein said inducing step is performed by a magnetically actuated stir bar, an entirety of said stir bar residing below a fluid line of said solvent, and said stir bar tapping an inner wall of said vessel to induce said resonant acoustic emission from said vessel;
   dissolving a known amount of the test material in the solvent; and
   measuring changes in resonance and absorbance frequencies of said resonant acoustic emission from said vessel before and after said dissolving step, a completion of said dissolving step being determined by a time point at which a resonant fundamental frequency curve of said resonance frequencies reaches approximately a minimum resonant frequency, said measuring step producing a broadband acoustic resonant dissolution emission profile, and said measuring step being performed by a microphone transducer removeably mounted on said vessel, said microphone transducer being positioned above said fluid line of said solvent.

2. A method according to claim 1 further comprising the step of comparing the test material broadband acoustic resonant dissolution emission profile to that of a known standard.

3. A method according to claim 1 wherein said solvent contains dissolved gas.

4. A method according to claim 3 wherein said dissolved gas is air.

5. A method according to claim 1 wherein said test material is a solid particulate or a liquid.

6. A method according to claim 1 wherein the amount of test material dissolved is sufficient to elicit an acoustic spectrum or to alter the acoustic spectrum of a standard.

7. A method according to claim 1 wherein said method is used to differentiate between hydrated species and mixtures thereof, material particle sizes, isomers and epimers.

8. An instrument for measuring the broadband acoustic resonance dissolution emission response of a test material comprising
   a dissolution vessel in which the test material can be dissolved in a solvent during a dissolution event, said dissolution vessel being made of a resonant material;
   means for inducing a resonant acoustic emission from the vessel;
   means for measuring the broadband acoustic resonance dissolution emission response of the dissolution vessel over the course of the dissolution event, the means for measuring being removeably mounted on said dissolution vessel above a fluid line of the solvent, and a completion of the dissolution event being determined by a time point at which a resonant fundamental frequency curve of resonance frequencies of said resonant acoustic emission from said vessel reaches approximately a minimum resonant frequency.

9. An instrument according to claim 8 further comprising a means to convert the acoustic dissolution emission response from acoustic to plot data.

10. An instrument according to claim 8 wherein said means for inducing resonant acoustic emission comprises a magnetically actuated stir bar, an entirety of said stir bar residing below said fluid line of said solvent, and said stir bar tapping an inner wall of said dissolution vessel to induce said resonant acoustic emission from said vessel.

11. An instrument as claimed in claim 8 wherein said means for measuring the broadband acoustic resonance dissolution emission response comprises a microphone transducer.

12. An instrument according to claim 8 wherein the vessel is glass or any resonant material.

13. A method of calibrating a broadband acoustic resonance dissolution emission instrument for use in a broadband acoustic resonance dissolution emission spectroscopic method comprising:
   inducing resonant acoustic emission from a vessel containing a solvent, said vessel being made of a resonant material, wherein said inducing step is performed by a magnetically actuated stir bar, an entirety of said stir bar residing below a fluid line of said solvent, and said stir bar tapping an inner wall of said vessel to induce said resonant acoustic emission from said vessel;
   dissolving at least one known amount of a test material in said vessel to produce a broadband acoustic resonance dissolution emission; and
   measuring changes to said broadband acoustic resonance dissolution emission of the vessel as the test material dissolves wherein the response is indicative of the amount of material dissolved, a completion of said dissolving step is determined by a time point at which a resonant fundamental frequency curve of said resonant acoustic emission from said vessel reaches approximately a minimum resonant frequency, and said measuring step is performed by a microphone transducer removeably mounted on said vessel, said microphone transducer being positioned above said fluid line of said solvent.

14. A method according to claim 13 wherein the resonant acoustic dissolution emission response is measured for at least two known amounts of the material.

15. A method according to claim 13 wherein the broadband acoustic resonance dissolution emission response is measured for at least three different known amounts of the material.

16. A method according to claim 13 wherein each of the broadband resonant acoustic dissolution emission responses is plotted against the amount of test material dissolved to produce a calibration curve.

17. A method according to claim 13 wherein the solvent is gas saturated.

18. A method according to claim 17 wherein said gas is argon, nitrogen or helium or other dissolvable gas.

19. A method according to claim 13 wherein said test material is a particulate.

20. A method according to claim 13 where the amount of test material dissolved is in the range appropriate to induce an acoustic profile.

* * * * *